United States Patent
Cheng et al.

(10) Patent No.: US 10,150,740 B2
(45) Date of Patent: Dec. 11, 2018

(54) 6,7-DIHYDROPYRIDO[2,1-A]PHTHALAZIN-2-ONES FOR THE TREATMENT AND PROPHYLAXIS OF HEPATITIS B VIRUS INFECTION

(71) Applicant: Hoffmann-La Roche Inc., Little Falls, NJ (US)

(72) Inventors: Zhanling Cheng, Shanghai (CN); Xingchun Han, Shanghai (CN); Yongguang Wang, Shanghai (CN); Song Yang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/866,429

(22) Filed: Jan. 9, 2018

(65) Prior Publication Data

US 2018/0127381 A1    May 10, 2018

Related U.S. Application Data

(63) Continuation of application No. PCT/EP2016/067609, filed on Jul. 25, 2016.

(30) Foreign Application Priority Data

Jul. 28, 2015  (WO) ................. PCT/CN2015/085265

(51) Int. Cl.
| | |
|---|---|
| *C07D 471/06* | (2006.01) |
| *A61K 31/5025* | (2006.01) |
| *C07D 237/26* | (2006.01) |
| *C07D 471/04* | (2006.01) |
| *A61P 31/20* | (2006.01) |

(52) U.S. Cl.
CPC ............ *C07D 237/26* (2013.01); *A61P 31/20* (2018.01); *C07D 471/04* (2013.01)

(58) Field of Classification Search
CPC .......................... C07D 471/06; A61K 31/5025
USPC .......................................... 544/234; 514/248
See application file for complete search history.

(56) References Cited

U.S. PATENT DOCUMENTS

2017/0342068 A1* 11/2017 Aktoudianakis et al. ...................
C07D 471/04
544/234

FOREIGN PATENT DOCUMENTS

| JP | S60197684 A | 7/1985 |
|---|---|---|
| WO | 2015/113990 A1 | 8/2015 |
| WO | 2015/173164 A1 | 11/2015 |
| WO | 2016/071215 A1 | 5/2016 |
| WO | 2016/128335 A1 | 8/2016 |

OTHER PUBLICATIONS

Fecik et al., "Chiral DNA gyrase inhibitors. 3. Probing the chiral preference of the active site of DNA gyrase. Synthesis of 10-fluoro-6-methyl-6,7-dihydro-9-piperazinyl-2H-benzo[a]quinolizin-20-one-3-carboxylic acid analogues" J Med Chem 48(4):1229-1236 ( 2005).
Geng et al., "Small-molecule inhibitors for the treatment of hepatitis B virus documented in patents" Mini Reviews in Medical Chemistry 13(5):749-776 (Apr. 1, 2013).
ISR for PCT/EP2016/067609 (Aug. 17, 2016).
Georgopapadakou et al., "Monocyclic and Tricyclic Analogs of Quinolones: Mechanism of Action" Antimicrobal Agents and Chemotherapy, 31(4):614-616 ( 1987).

* cited by examiner

*Primary Examiner* — Charanjit Aulakh
(74) *Attorney, Agent, or Firm* — Brian L. Buckwalter

(57) ABSTRACT

The invention provides novel compounds having the general formula:

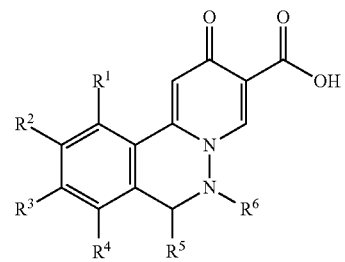

wherein $R^1$ to $R^6$ are as described herein, compositions including the compounds and methods of using the compounds.

15 Claims, No Drawings

6,7-DIHYDROPYRIDO[2,1-A]PHTHALAZIN-2-ONES FOR THE TREATMENT AND PROPHYLAXIS OF HEPATITIS B VIRUS INFECTION

CROSS REFERENCE TO RELATED APPLICATIONS

This application is a continuation of International Application No. PCT/EP2016/067609 having an international filing date Jul. 25, 2016 and which claims benefit under 35 U.S.C. § 119 to International Application No. PCT/CN2015/085265 having an international filing date of Jul. 28, 2015. The entire contents of both are incorporated herein by reference.

FIELD OF THE INVENTION

The present invention relates to organic compounds useful for therapy and/or prophylaxis in a mammal, and in particular to HBsAg (HBV Surface antigen) inhibitors and HBV DNA production inhibitors useful for treating HBV infection.

The present invention relates to novel 6,7-dihydropyrido[2,1-a]phthalazin-2-ones compounds of formula (I) having pharmaceutical activity, their manufacture, pharmaceutical compositions containing them and their potential use as medicaments.

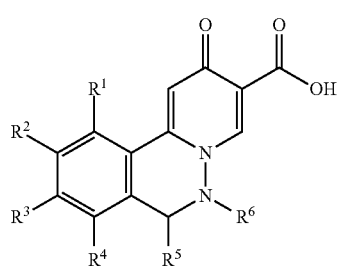

(I)

wherein $R^1$ to $R^6$ are as described below, or to a pharmaceutically acceptable salt, or an enantiomers, or a diastereomer thereof.

BACKGROUND OF THE INVENTION

The hepatitis B virus (HBV) is an enveloped, partially double-stranded DNA virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORF. The lifecycle of HBV has two main events: 1) generation of closed circular DNA (cccDNA) from relaxed circular (RC DNA), and 2) reverse transcription of pregenomic RNA (pgRNA) to produce RC DNA. Prior to the infection of host cells, the HBV genome exists within the virion as RC DNA. It has been determined that HBV virions are able to gain entry into host cells by non-specifically binding to the negatively charged proteoglycans present on the surface of human hepatocytes (Schulze, A., P. Gripon & S. Urban. *Hepatology*, 46, (2007), 1759-68) and via the specific binding of HBV surface antigens (HBsAg) to the hepatocyte sodium-taurocholate cotransporting polypeptide (NTCP) receptor (Yan, H. et al. *J Virol*, 87, (2013), 7977-91). Once the virion has entered the cell, the viral cores and the encapsidated RC DNA are transported by host factors, via a nuclear localization signal, into the nucleus through the Impβ/Impα nuclear transport receptors. Inside the nucleus, host DNA repair enzymes convert the RC DNA into cccDNA. cccDNA acts as the template for all viral mRNAs and as such, is responsible for HBV persistence in infected individuals. The transcripts produced from cccDNA are grouped into two categories; Pregenomic RNA (pgRNA) and subgenomic RNA. Subgenomic transcripts encode for the three envelopes (L, M and S) and X proteins, and pgRNA encodes for Pre-Core, Core, and Pol proteins (Quasdorff, M. & U. Protzer. *J Viral Hepat*, 17, (2010), 527-36). Inhibition of HBV gene expression or HBV RNA synthesis leads to the inhibition of HBV viral replication and antigens production (Mao, R. et al. *PLoS Pathog*, 9, (2013), e1003494; Mao, R. et al. *J Virol*, 85, (2011), 1048-57). For instance, IFN-α was shown to inhibit HBV replication and viral HBsAg production by decreasing the transcription of pgRNA and subgenomic RNA from the HBV covalently closed circular DNA (cccDNA) minichromosome. (Belloni, L. et al. *J Clin Invest*, 122, (2012), 529-37; Mao, R. et al. *J Virol*, 85, (2011), 1048-57). All HBV viral mRNAs are capped and polyadenylated, and then exported to the cytoplasm for translation. In the cytoplasm, the assembly of new virons is initiated and nascent pgRNA is packaged with viral Pol so that reverse transcription of pgRNA, via a single stranded DNA intermediate, into RC DNA can commence. The mature nucleocapsids containing RC DNA are enveloped with cellular lipids and viral L, M, and S proteins and then the infectious HBV particles are then released by budding at the intracellular membrane (Locarnini, S. *Semin Liver Dis*, (2005), 25 Suppl 1, 9-19). Interestingly, non-infectious particles are also produced that greatly outnumber the infectious virions. These empty, enveloped particles (L, M and S) are referred to as subviral particles. Importantly, since subviral particles share the same envelope proteins and as infectious particles, it has been surmised that they act as decoys to the host immune system and have been used for HBV vaccines. The S, M, and L envelope proteins are expressed from a single ORF that contains three different start codons. All three proteins share a 226aa sequence, the S-domain, at their C-termini. M and L have additional pre-S domains, Pre-S2 and Pre-S2 and Pre-S1, respectively. However, it is the S-domain that has the HBsAg epitope (Lambert, C. & R. Prange. *Virol J*, (2007), 4, 45).

The control of viral infection needs a tight surveillance of the host innate immune system which could respond within minutes to hours after infection to impact on the initial growth of the virus and limit the development of a chronic and persistent infection. Despite the available current treatments based on IFN and nucleos(t)ide analogues, the Hepatitis B virus (HBV) infection remains a major health problem worldwide which concerns an estimated 350 million chronic carriers who have a higher risk of liver cirrhosis and hepatocellular carcinoma.

The secretion of antiviral cytokines in response to HBV infection by the hepatocytes and/or the intra-hepatic immune cells plays a central role in the viral clearance of infected liver. However, chronically infected patients only display a weak immune response due to various escape strategies adopted by the virus to counteract the host cell recognition systems and the subsequent antiviral responses.

Many observations showed that several HBV viral proteins could counteract the initial host cellular response by interfering with the viral recognition signaling system and subsequently the interferon (IFN) antiviral activity. Among these, the excessive secretion of HBV empty subviral particles (SVPs, HBsAg) may participate to the maintenance of the immunological tolerant state observed in chronically infected patients (CHB). The persistent exposure to HBsAg and other viral antigens can lead to HBV-specific T-cell deletion or to progressive functional impairment (Kondo et al. *Journal of Immunology* (1993), 150, 4659-4671; Kondo et al. *Journal of Medical Virology* (2004), 74, 425-433; Fisicaro et al. *Gastroenterology*, (2010), 138, 682-93). Moreover HBsAg has been reported to suppress the function of immune cells such as monocytes, dendritic cells (DCs) and natural killer (NK) cells by direct interaction (Op den Brouw et al. *Immunology*, (2009b), 126, 280-9; Woltman et al. *PLoS One*, (2011), 6, e15324; Shi et al. *J Viral Hepat.* (2012), 19, e26-33; Kondo et al. *ISRN Gasteroenterology*, (2013), Article ID 935295).

HBsAg quantification is a significant biomarker for prognosis and treatment response in chronic hepatitis B. However the achievement of HBsAg loss and seroconversion is rarely observed in chronically infected patients but remains the ultimate goal of therapy. Current therapy such as Nucleos(t)ide analogues are molecules that inhibit HBV DNA synthesis but are not directed at reducing HBsAg level. Nucleos(t)ide analogs, even with prolonged therapy, have demonstrated rates of HBsAg clearance comparable to those observed naturally (between –1%-2%) (Janssen et al. *Lancet*, (2005), 365, 123-9; Marcellin et al. *N. Engl. J. Med.*, (2004), 351, 1206-17; Buster et al. *Hepatology*, (2007), 46, 388-94). Therefore, there is an unmet medical need to target HBsAg for HBV treatment (Wieland, S. F. & F. V. Chisari. *J Virol*, (2005), 79, 9369-80; Kumar et al. *J Virol*, (2011), 85, 987-95; Woltman et al. *PLoS One*, (2011), 6, e15324; Op den Brouw et al. *Immunology*, (2009b), 126, 280-9).

SUMMARY OF THE INVENTION

Objects of the present invention are novel compounds of formula I, their manufacture, medicaments based on a compound in accordance with the invention and their production as well as the use of compounds of formula I as HBV inhibitors and for the treatment or prophylaxis of HBV infection. The compounds of formula I show superior anti-HBV activity.

The present invention relates to a compound of formula I

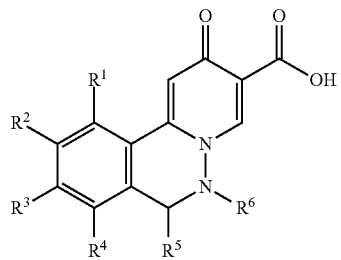

(I)

wherein
$R^1$, $R^2$, $R^3$ and $R^4$ are independently selected from $C_{1-6}$alkyl, halo$C_{1-6}$alkyl, hydrogen, halogen, amino, cyano, pyrrolidinyl, hydroxy, $C_{1-6}$alkoxy, halo$C_{1-6}$alkoxy, $C_{3-7}$cycloalkyl $C_{1-6}$alkyloxy, phenyl$C_{1-6}$alkyloxy, hydroxy$C_{1-6}$alkyloxy, $C_{1-6}$alkoxy$C_{1-6}$alkyloxy, $C_{1-6}$alkylsulfanyl$C_{1-6}$alkyloxy, $C_{1-6}$alkylsulfonyl$C_{1-6}$alkyloxy, cyano$C_{1-6}$alkyloxy, amino$C_{1-6}$alkyloxy, $C_{1-6}$alkylamino$C_{1-6}$alkyloxy, di$C_{1-6}$alkylamino$C_{1-6}$alkyloxy, $C_{1-6}$alkylcarbonylamino$C_{1-6}$alkyloxy, $C_{1-6}$alkylsulfonylamino$C_{1-6}$alkyloxy, $C_{1-6}$alkoxycarbonylamino$C_{1-6}$alkyloxy, pyrazolyl$C_{1-6}$alkyloxy, triazolyl$C_{1-6}$alkyloxy and monocyclic heterocycloalkyl$C_{1-6}$alkyloxy, wherein monocyclic heterocycloalkyl is N-containing monocyclic heterocycloalkyl;
$R^5$ and $R^6$ are independently selected from hydrogen, $C_{1-6}$alkyl, halo$C_{1-6}$alkyl or $C_{2-6}$alkenyl; or pharmaceutically acceptable salts, or enantiomers, or diastereomer thereof.

DETAILED DESCRIPTION OF THE INVENTION

Definitions

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl and tert-butyl.

The term "$C_{2-6}$alkenyl" denotes a monovalent linear or branched hydrocarbon group of 2 to 6 carbon atoms with at least one double bond. In particular embodiments, $C_{1-6}$alkenyl has 2 to 4 carbon atoms with at least one double bond. Examples of alkenyl include ethenyl, propenyl, prop-2-enyl, isopropenyl, n-butenyl, and iso-butenyl. Particular "$C_{1-6}$alkyl" group is prop-2-enyl.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" groups are cyclopropyl, cyclobutyl, cyclopentyl and cyclohexyl.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy, pentoxy, hexyloxy, octyloxy and the like. Particular "$C_{1-6}$alkoxy" groups are methoxy, ethoxy and propoxy.

The term "halogen" means fluorine, chlorine, bromine or iodine.

The term "halo$C_{1-6}$alkyl" denotes a $C_{1-6}$alkyl group wherein at least one of the hydrogen atoms of the $C_{1-6}$alkyl group has been replaced by same or different halogen atoms, particularly fluoro atoms. Examples of halo$C_{1-6}$alkyl include monofluoro-, difluoro- or trifluoro-methyl, -ethyl or -propyl, for example 3,3,3-trifluoropropyl, 3,3-difluoropropyl, 2-fluoroethyl, 2,2-difluoroethyl, 2,2,2-trifluoroethyl, fluoromethyl, difluoromethyl or trifluoromethyl. Particular "halo$C_{1-6}$alkyl" group is difluoromethyl or trifluoromethyl.

The term "halo$C_{1-6}$alkoxy" denotes a $C_{1-6}$alkoxy group wherein at least one of the hydrogen atoms of the $C_{1-6}$alkoxy group has been replaced by same or different halogen atoms, particularly fluoro atoms. Examples of halo$C_{1-6}$alkoxyl include monofluoro-, difluoro- or trifluoro-methoxy, -ethoxy or -propoxy, for example fluoropropoxy, difluoropropoxy, trifluoropropoxy, fluoroethoxy, difluoroethoxy, trifluoroethoxy, fluoromethoxy, difluoromethoxy or trifluoromethoxy. Particular "halo$C_{1-6}$alkoxy" group is 3-fluoropropoxy, 3,3-difluoropropoxy, 3,3,3-trifluoropropoxy, 2-fluoroethoxy, 2,2-difluoroethoxy, 2,2,2-trifluoroethoxy, fluoromethoxy, difluoromethoxy or trifluoromethoxy.

The term "amino" denotes a group of the formula —NR'R" wherein R' and R" are independently hydrogen, $C_{1-6}$alkyl, $C_{1-6}$alkoxy, $C_{3-7}$cycloalkyl, hetero$C_{3-7}$cycloalkyl, aryl or heteroaryl. Alternatively, R' and R", together with the nitrogen to which they are attached, can form a hetero$C_{3-7}$cycloalkyl.

The term "carbonyl" alone or in combination refers to the group —C(O)—.

The term "cyano" alone or in combination refers to the group —CN.

The term "$C_{1-6}$alkylsulfanyl" denotes the group —S—R', wherein R' is a $C_{1-6}$alkyl group as defined above. Examples of $C_{1-6}$alkylsulfanyl include methylsulfanyl and ethylsulfanyl.

The term "$C_{1-6}$alkylsulfonyl" denotes a group —SO$_2$—R', wherein R' is a $C_{1-6}$alkyl group as defined above. Examples of $C_{1-6}$alkylsulfonyl include methylsulfonyl and ethylsulfonyl.

The term "monocyclic heterocycloalkyl" is a monovalent saturated or partly unsaturated monocyclic ring system of 4 to 7 ring atoms, comprising 1, 2, or 3 ring heteroatoms selected from N, O and S, the remaining ring atoms being carbon. Examples for monocyclic heterocycloalkyl are aziridinyl, oxiranyl, azetidinyl, oxetanyl, pyrrolidinyl, 2-oxo-pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, 2-oxo-morpholinyl, 2-oxo-piperazinyl, thiomorpholinyl, 1,1-dioxo-thiomorpholin-4-yl, 1,1-dioxothiolanyl, azepanyl, diazepanyl, homopiperazinyl, or oxazepanyl. Particular "monocyclic heterocycloalkyl" groups are oxetanyl, tetrahydrofuranyl, tetrahydropyranyl, 1,1-dioxothiolanyl, morpholinyl, 2-oxo-pyrrolidinyl, 2-oxo-morpholinyl and 2-oxo-piperazinyl.

The term "N-containing monocyclic heterocycloalkyl" refers to a monocyclic heterocycloalkyl wherein at least one of the heteroatoms is N. Examples for N-containing monocyclic heterocycloalkyl are azetidinyl, pyrrolidinyl, pyrazolidinyl, imidazolidinyl, oxazolidinyl, isoxazolidinyl, thiazolidinyl, piperidinyl, piperazinyl, morpholinyl, azepanyl, diazepanyl, homopiperazinyl or oxazepanyl. Particular "N-containing monocyclic heterocycloalkyl" groups are pyrrolidinyl, 2-oxo-pyrrolidinyl, piperidinyl, piperazinyl, tetrahydropyranyl and morpholinyl, and more particularly tetrahydropyranyl and morpholinyl.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435. Particular are the sodium salts of the compounds of formula I.

Compounds of the general formula I which contain one or several chiral centers can either be present as racemates, diastereomeric mixtures, or optically active single isomers.

The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitor of HBsAg

The present invention provides (i) a compound having the general formula I:

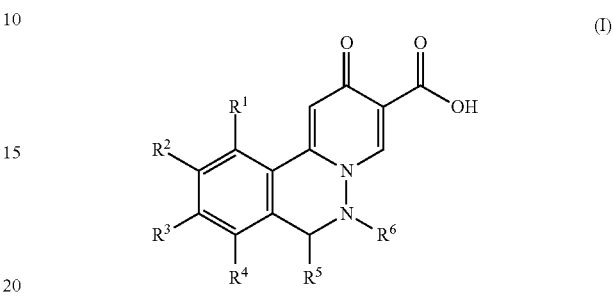

(I)

wherein
$R^1$, $R^2$, $R^3$ and $R^4$ are independently selected from $C_{1-6}$alkyl, halo$C_{1-6}$alkyl, hydrogen, halogen, amino, cyano, pyrrolidinyl, hydroxy, $C_{1-6}$alkoxy, halo$C_{1-6}$alkoxy, $C_{3-7}$cycloalkyl $C_{1-6}$alkyloxy, phenyl$C_{1-6}$alkyloxy, hydroxy$C_{1-6}$alkyloxy, $C_{1-6}$alkoxy$C_{1-6}$alkyloxy, $C_{1-6}$alkylsulfanyl$C_{1-6}$alkyloxy, $C_{1-6}$alkylsulfonyl$C_{1-6}$alkyloxy, cyano$C_{1-6}$alkyloxy, amino$C_{1-6}$alkyloxy, $C_{1-6}$alkylamino$C_{1-6}$alkyloxy, di$C_{1-6}$alkylamino$C_{1-6}$alkyloxy, $C_{1-6}$alkylcarbonylamino$C_{1-6}$alkyloxy, $C_{1-6}$alkylsulfonylamino$C_{1-6}$alkyloxy, $C_{1-6}$alkoxycarbonylamino$C_{1-6}$alkyloxy, pyrazolyl$C_{1-6}$alkyloxy, triazolyl$C_{1-6}$alkyloxy and monocyclic heterocycloalkyl$C_{1-6}$alkyloxy, wherein monocyclic heterocycloalkyl is N-containing monocyclic heterocycloalkyl;
$R^5$ and $R^6$ are independently selected from hydrogen, $C_{1-6}$alkyl, halo$C_{1-6}$alkyl or $C_{2-6}$alkenyl; or pharmaceutically acceptable salts, or enantiomers, or diastereomer thereof.

Another embodiment of present invention is (ii) a compound of formula I, wherein
$R^1$ is hydrogen;
$R^2$ is $C_{1-6}$alkoxy;
$R^3$ is $C_{1-6}$alkoxy, halo$C_{1-6}$alkoxy, hydroxy$C_{1-6}$alkoxy, $C_{1-6}$alkoxy$C_{1-6}$alkoxy, $C_{1-6}$alkylsulfonyl$C_{1-6}$alkoxy, cyano$C_{1-6}$alkoxy, carboxy$C_{1-6}$alkoxy, amino$C_{1-6}$alkoxy, $C_{1-6}$alkoxycarbonylamino$C_{1-6}$alkoxy, morpholinyl$C_{1-6}$alkoxy or tetrahydropyranyl$C_{1-6}$alkoxy;
$R^4$ is hydrogen;
$R^5$ is hydrogen;
$R^6$ is hydrogen, $C_{1-6}$alkyl or $C_{2-6}$alkenyl;
or pharmaceutically acceptable salts, or enantiomers, or diastereomer thereof.

A further embodiment of present invention is (iii) a compound of formula I, wherein
$R^1$ is hydrogen;
$R^2$ is methoxy;
$R^3$ methoxy, trifluoroethoxy, hydroxydimethylpropoxy, methoxypropoxy, methylsulfonylpropoxy, cyanopropoxy, carboxybutoxy, aminopentoxy, tert-butoxycarbonylaminopentoxy, morpholinylethoxy or tetrahydropyranylmethoxy;
$R^4$ is hydrogen;
$R^5$ is hydrogen;
$R^6$ is hydrogen, methyl, isopropyl, isobutyl or prop-2-enyl;
or pharmaceutically acceptable salts, or enantiomers, or diastereomer thereof.

Another embodiment of present invention is (iv) a compound of formula I or pharmaceutically acceptable salts, or enantiomers, or diastereomer thereof, wherein $R^2$ is methoxy, and all remaining substituents have the significances given herein before.

Another embodiment of present invention is (v) a compound of formula I or pharmaceutically acceptable salts, or enantiomers, or diastereomer thereof, wherein $R^3$ is haloC$_{1-6}$alkoxy, hydroxyC$_{1-6}$alkoxy, C$_{1-6}$alkoxyC$_{1-6}$alkoxy, cyanoC$_{1-6}$alkoxy, C$_{1-6}$alkoxycarbonylaminoC$_{1-6}$alkoxy or tetrahydropyranylC$_{1-6}$alkoxy, and all remaining substituents have the significances given herein before.

A further embodiment of present invention is (vi) a compound of formula I or pharmaceutically acceptable salts, or enantiomers, or diastereomer thereof, wherein $R^3$ is trifluoroethoxy, hydroxydimethylpropoxy, methoxypropoxy, cyanopropoxy, tert-butoxycarbonylaminopentoxy, or tetrahydropyranylmethoxy, and all remaining substituents have the significances given herein before.

Another embodiment of present invention is (vii) a compound of formula I or pharmaceutically acceptable salts, or enantiomers, or diastereomer thereof, wherein $R^6$ is C$_{1-6}$alkyl, and all remaining substituents have the significances given herein before.

A further embodiment of present invention is (viii) a compound of formula I or pharmaceutically acceptable salts, or enantiomers, or diastereomer thereof, wherein $R^6$ is isobutyl, and all remaining substituents have the significances given herein before.

Particular compounds of formula I according to the invention are the following:
9,10-Dimethoxy-2-oxo-6,7-dihydropyrido[2,1-a]phthalazine-3-carboxylic acid;
9,10-Dimethoxy-6-methyl-2-oxo-7H-pyrido[2,1-a]phthalazine-3-carboxylic acid;
6-Allyl-9,10-dimethoxy-2-oxo-7H-pyrido[2,1-a]phthalazine-3-carboxylic acid;
6-Isopropyl-9,10-dimethoxy-2-oxo-7H-pyrido[2,1-a]phthalazine-3-carboxylic acid;
6-Isobutyl-9,10-dimethoxy-2-oxo-7H-pyrido[2,1-a]phthalazine-3-carboxylic acid;
6-Isobutyl-10-methoxy-9-(3-methoxypropoxy)-2-oxo-7H-pyrido[2,1-a]phthalazine-3-carboxylic acid;
6-Isobutyl-10-methoxy-2-oxo-9-(2,2,2-trifluoroethoxy)-7H-pyrido[2,1-a]phthalazine-3-carboxylic acid;
6-Isobutyl-10-methoxy-2-oxo-9-(tetrahydropyran-4-ylmethoxy)-7H-pyrido[2,1-a]phthalazine-3-carboxylic acid;
6-Isobutyl-10-methoxy-9-(3-methylsulfonylpropoxy)-2-oxo-7H-pyrido[2,1-a]phthalazine-3-carboxylic acid;
6-Isobutyl-10-methoxy-9-(2-morpholinoethoxy)-2-oxo-7H-pyrido[2,1-a]phthalazine-3-carboxylic acid;
9-(3-Hydroxy-2,2-dimethyl-propoxy)-6-isobutyl-10-methoxy-2-oxo-7H-pyrido[2,1-a]phthalazine-3-carboxylic acid;
9-(4-Carboxybutoxy)-6-isobutyl-10-methoxy-2-oxo-7H-pyrido[2,1-a]phthalazine-3-carboxylic acid;
9-(3-Cyanopropoxy)-6-isobutyl-10-methoxy-2-oxo-7H-pyrido[2,1-a]phthalazine-3-carboxylic acid;
9-[5-(Tert-butoxycarbonylamino)pentoxy]-6-isobutyl-10-methoxy-2-oxo-7H-pyrido[2,1-a]phthalazine-3-carboxylic acid;
9-(5-Aminopentoxy)-6-isobutyl-10-methoxy-2-oxo-7H-pyrido[2,1-a]phthalazine-3-carboxylic acid hydrochloride
or pharmaceutically acceptable salts, or enantiomers, or diastereomer thereof.

10. A compound according to claim 1, selected from
6-Isobutyl-10-methoxy-9-(3-methoxypropoxy)-2-oxo-7H-pyrido[2,1-a]phthalazine-3-carboxylic acid;
6-Isobutyl-10-methoxy-2-oxo-9-(tetrahydropyran-4-ylmethoxy)-7H-pyrido[2,1-a]phthalazine-3-carboxylic acid;
9-(3-Hydroxy-2,2-dimethyl-propoxy)-6-isobutyl-10-methoxy-2-oxo-7H-pyrido[2,1-a]phthalazine-3-carboxylic acid;
9-[5-(Tert-butoxycarbonylamino)pentoxy]-6-isobutyl-10-methoxy-2-oxo-7H-pyrido[2,1-a]phthalazine-3-carboxylic acid;
or pharmaceutically acceptable salts, or enantiomers, or diastereomer thereof.

More particularly, the invention relates to the following compounds of formula I:
6-Isobutyl-10-methoxy-9-(3-methoxypropoxy)-2-oxo-7H-pyrido[2,1-a]phthalazine-3-carboxylic acid;
6-Isobutyl-10-methoxy-2-oxo-9-(tetrahydropyran-4-ylmethoxy)-7H-pyrido[2,1-a]phthalazine-3-carboxylic acid;
9-(3-Hydroxy-2,2-dimethyl-propoxy)-6-isobutyl-10-methoxy-2-oxo-7H-pyrido[2,1-a]phthalazine-3-carboxylic acid;
9-[5-(Tert-butoxycarbonylamino)pentoxy]-6-isobutyl-10-methoxy-2-oxo-7H-pyrido[2,1-a]phthalazine-3-carboxylic acid;
or pharmaceutically acceptable salts, or enantiomers, or diastereomer thereof.

Synthesis

The compounds of the present invention can be prepared by any conventional means. Suitable processes for synthesizing these compounds as well as their starting materials are provided in the schemes below and in the examples. All substituents, in particular, $R^1$ to $R^6$ are as defined above unless otherwise indicated. Furthermore, and unless explicitly otherwise stated, all reactions, reaction conditions, abbreviations and symbols have the meanings well known to a person of ordinary skill in organic chemistry.

General Synthetic Route for Intermediates (Scheme 1)

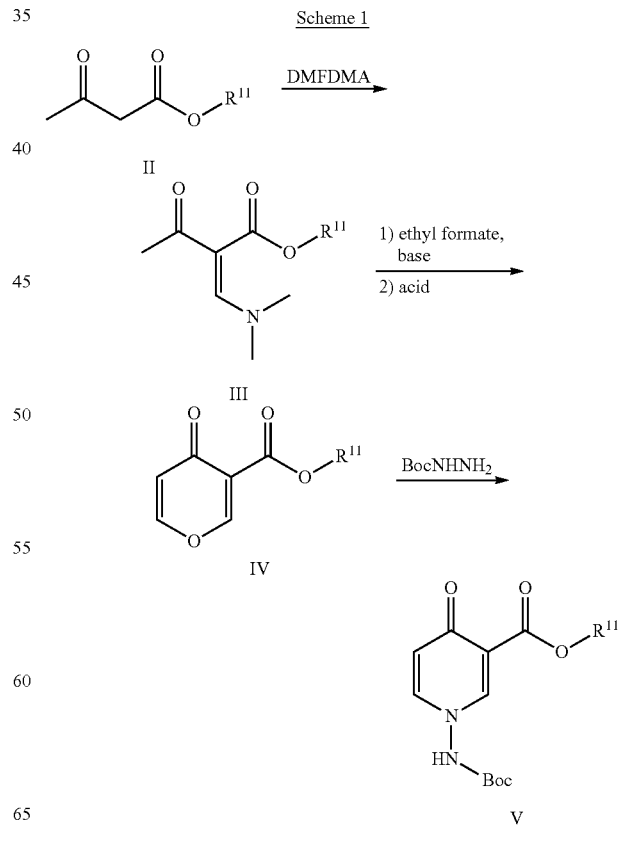

The intermediate of formula V can be prepared according to Scheme 1. Compound II reacts with DMFDMA at a temperature between 0 and 80° C. to afford compound III, which reacts with ethyl formate in the presence of a base such as t-BuOK, and then the resulting reaction mixture is treated with an acid such as hydrochloric acid to afford compound IV. Compound IV reacts with tert-butyl N-aminocarbamate in a suitable solvent such as EtOH at a temperature between rt and 100° C. to give compound V.

General Synthetic Route for Compounds I (Scheme 2)

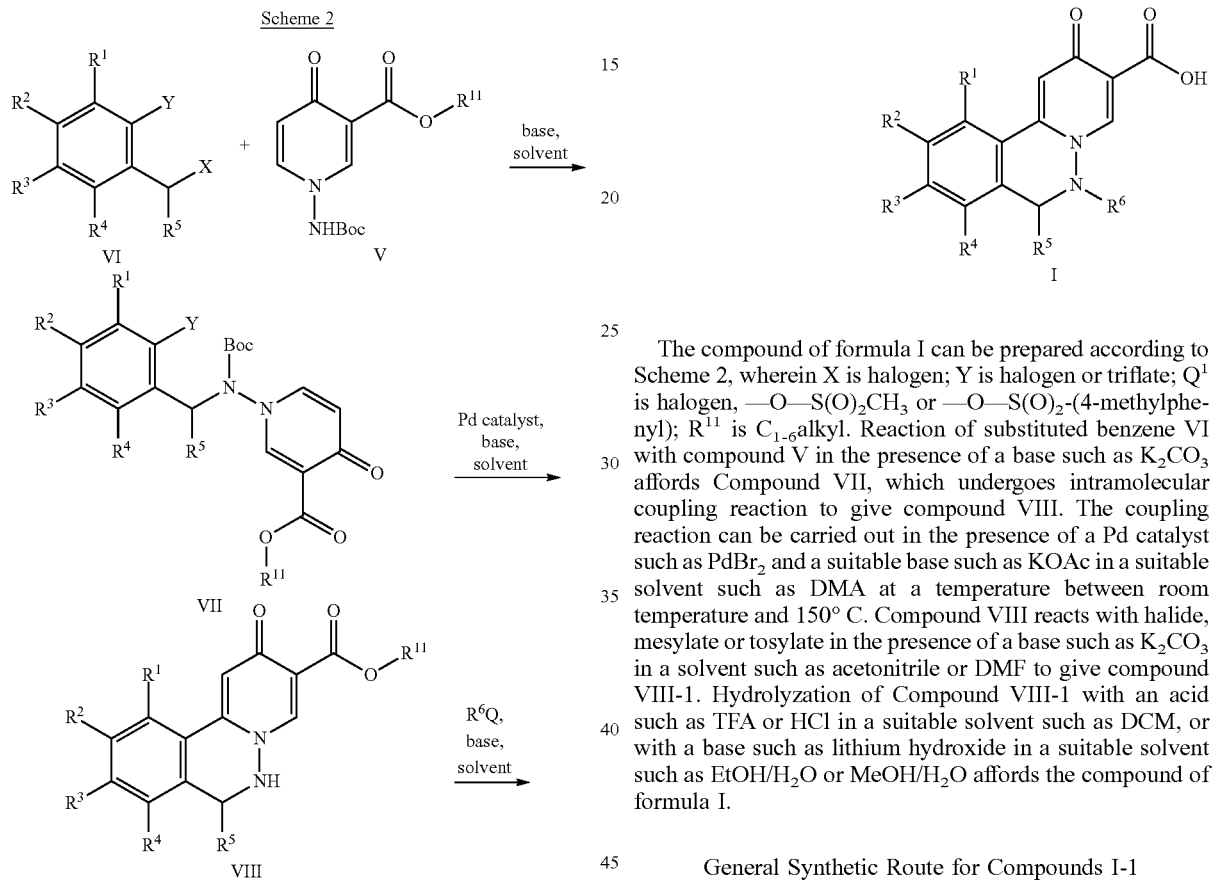

The compound of formula I can be prepared according to Scheme 2, wherein X is halogen; Y is halogen or triflate; $Q^1$ is halogen, —O—S(O)$_2$CH$_3$ or —O—S(O)$_2$-(4-methylphenyl); $R^{11}$ is $C_{1-6}$alkyl. Reaction of substituted benzene VI with compound V in the presence of a base such as K$_2$CO$_3$ affords Compound VII, which undergoes intramolecular coupling reaction to give compound VIII. The coupling reaction can be carried out in the presence of a Pd catalyst such as PdBr$_2$ and a suitable base such as KOAc in a suitable solvent such as DMA at a temperature between room temperature and 150° C. Compound VIII reacts with halide, mesylate or tosylate in the presence of a base such as K$_2$CO$_3$ in a solvent such as acetonitrile or DMF to give compound VIII-1. Hydrolyzation of Compound VIII-1 with an acid such as TFA or HCl in a suitable solvent such as DCM, or with a base such as lithium hydroxide in a suitable solvent such as EtOH/H$_2$O or MeOH/H$_2$O affords the compound of formula I.

General Synthetic Route for Compounds I-1 (Scheme 3)

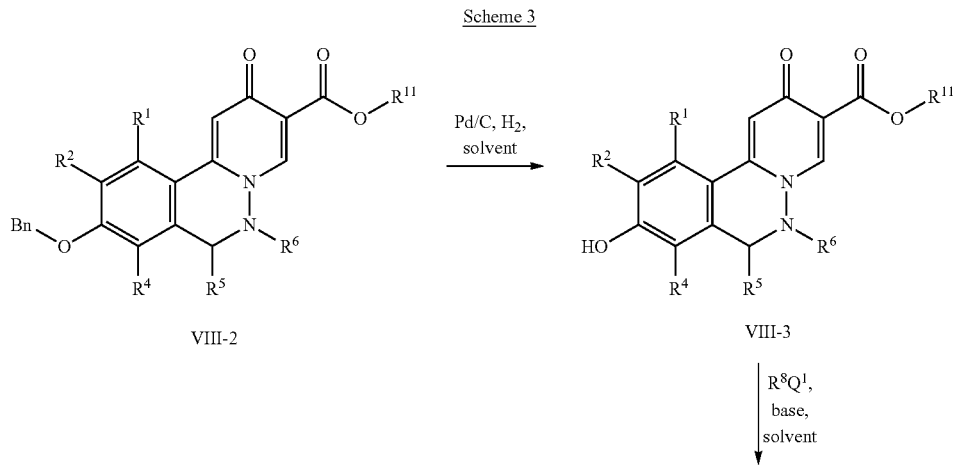

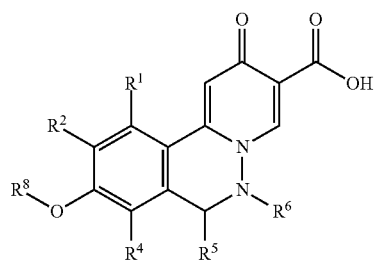

I-1

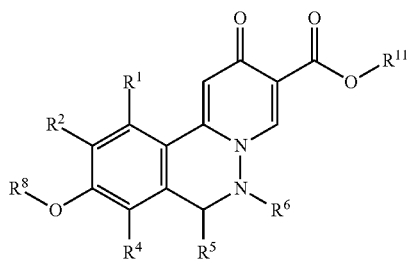

VIII-4

The compound of formula I-1 can be prepared according to Scheme 3, wherein $Q^1$ is halogen, —O—S(O)$_2$CH$_3$ or —O—S(O)$_2$-(4-methylphenyl); $R^8$ is $C_{1-6}$alkyl, haloC$_{1-6}$alkyl, $C_{3-7}$cycloalkylC$_{1-6}$alkyl, phenylC$_{1-6}$alkyl, hydroxyC$_{1-6}$alkyl, $C_{1-6}$alkoxyC$_{1-6}$alkyl, $C_{1-6}$alkylsulfanylC$_{1-6}$alkyl, $C_{1-6}$alkylsulfonylC$_{1-6}$alkyl, cyanoC$_{1-6}$alkyl, aminoC$_{1-6}$alkyl, $C_{1-6}$alkylaminoC$_{1-6}$alkyl, diC$_{1-6}$alkylaminoC$_{1-6}$alkyl, $C_{1-6}$alkylcarbonylaminoC$_{1-6}$alkyl, $C_{1-6}$alkylsulfonylaminoC$_{1-6}$alkyl, $C_{1-6}$alkoxycarbonylaminoC$_{1-6}$alkyl, pyrazolylC$_{1-6}$alkyl, triazolylC$_{1-6}$alkyl or monocyclic heterocycloalkylC$_{1-6}$alkyl, wherein monocyclic heterocycloalkyl is N-containing monocyclic heterocycloalkyl; $R^{11}$ is $C_{1-6}$alkyl. Debenzylation of Compound VIII-2 by hydrogenation is carried out in the presence of Pd/C in a solvent such as ethanol to afford Compound VIII-3. Then Compound VIII-3 reacts with halide, mesylate or tosylate in the presence of a base such as K$_2$CO$_3$ in a solvent such as DMF to give VIII-4. Hydrolyzation of Compound VIII-4 with an acid such as TFA or HCl in a suitable solvent such as DCM, or with a base such as lithium hydroxide in a suitable solvent such as EtOH/H$_2$O or MeOH/H$_2$O affords the compound of formula I.

This invention also relates to a process for the preparation of a compound of formula I comprising (a) hydrolysis of a compound of formula (A) by using an acid or a base

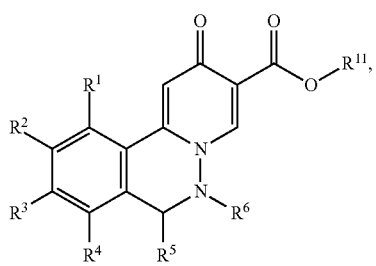

(A)

or (b) hydrolysis of a compound of formula (B) by using an acid or a base

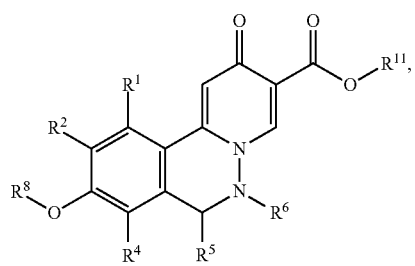

(B)

wherein $R^1$ to $R^6$, $R^8$ and $R^{11}$ are defined as above unless otherwise indicated.

In step (a) and (b), an acid is for example TFA or HCl; or a base is for example lithium hydroxide or sodium hydroxide.

A compound of formula I when manufactured according to the above process is also an object of the invention.

The invention also relates to a compound of formula I for use as therapeutically active substance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit HBsAg. For example, such amount may be below the amount that is toxic to normal cells, or the mammal as a whole.

In one example, the pharmaceutically effective amount of the compound of the invention administered parenterally per dose will be in the range of about 0.01 to 100 mg/kg, alternatively about 0.01 to 100 mg/kg of patient body weight per day, with the typical initial range of compound used being 0.3 to 15 mg/kg/day. In another embodiment, oral unit dosage forms, such as tablets and capsules, preferably contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 to 1000 mg of the compound of the invention compounded with about 0 to 2000 mg anhydrous lactose, about 0 to 2000 mg sodium croscarmellose, about 0 to 2000 mg polyvinylpyrrolidone (PVP) K30, and about 0 to 2000 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 0.1 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

The following example A and B illustrate typical compositions of the present invention, but serve merely as representative thereof.

Example A

A compound of formula I can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Indications and Methods of Treatment

The compounds of the invention can inhibit HBsAg production or secretion and inhibit HBV gene expression. Accordingly, the compounds of the invention are useful for the treatment or prophylaxis of HBV infection.

The invention relates to the use of a compound of formula I for the inhibition of HBsAg production or secretion.

The invention relates to the use of a compound of formula I for the inhibition of HBV DNA production.

The invention relates to the use of a compound of formula I for the inhibition of HBV gene expression.

The invention relates to the use of a compound of formula I for the treatment or prophylaxis of HBV infection.

The use of a compound of formula I for the preparation of medicaments useful in the treatment or prophylaxis diseases that are related to HBV infection is an object of the invention.

The invention relates in particular to the use of a compound of formula I for the preparation of a medicament for the treatment or prophylaxis of HBV infection.

Another embodiment includes a method for the treatment or prophylaxis of HBV infection, which method comprises administering an effective amount of a compound of Formula I, a stereoisomer, tautomer, prodrug, conjugates or pharmaceutically acceptable salt thereof.

EXAMPLES

The invention will be more fully understood by reference to the following examples. They should not, however, be construed as limiting the scope of the invention.

Abbreviations used herein are as follows:
μL: microliter
μm: micrometer
μM: micromoles per liter
DMF: dimethylformamide
DMFDMA: N,N-dimethylformamide dimethyl acetal
DMA: N,N-Dimethylaniline
DMSO-d6: deuterated dimethylsulfoxide
EtOAc: ethyl acetate
h or hr: hour
hrs: hours
$IC_{50}$: the half maximal inhibitory concentration
HPLC: high performance liquid chromatography
LC/MS: Liquid chromatography/mass spectrometry
METHANOL-$d_4$: perdeuteromethanol
M: molarity
mg: milligram
MHz: megahertz
min: minute
mL: milliliter
mM: millimoles per liter
mm: millimeter mmol: millimole
MS (ESI): mass spectroscopy (electron spray ionization)
NMR: nuclear magnetic resonance
N₂: nitrogen
rt: room temperature
Pd/C: palladium on activated carbon
prep-HPLC: preparative high performance liquid chromatography
TFA: trifluoroacetic acid
δ: chemical shift
t-BuOK: potassium tert-butylate General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp C₁₈ (5 μm, OBD™ 30×100 mm) column or SunFire™ Perp C₁₈ (5 μm, OBD™ 30×100 mm) column.

LC/MS spectra were obtained using an Acquity Ultra Performance LC-3100 Mass Detector or Acquity Ultra Performance LC-SQ Detector. Standard LC/MS conditions were as follows (running time 3 minutes):

Acidic condition: A: 0.1% formic acid in H₂O; B: 0.1% formic acid in acetonitrile;

Basic condition: A: 0.05% NH₃.H₂O in H₂O; B: acetonitrile;

Neutral condition: A: H₂O; B: acetonitrile.

Mass spectra (MS): generally only ions which indicate the parent mass are reported, and unless otherwise stated the mass ion quoted is the positive mass ion (M+H)⁺.

The microwave assisted reactions were carried out in a Biotage Initiator Sixty or CEM Discover.

NMR Spectra were obtained using Bruker Avance 400 MHz.

All reactions involving air-sensitive reagents were performed under an argon atmosphere. Reagents were used as received from commercial suppliers without further purification unless otherwise noted.

Preparative Examples

Example 1: 9,10-Dimethoxy-2-oxo-6,7-dihydropyrido[2,1-a]phthalazine-3-carboxylic acid

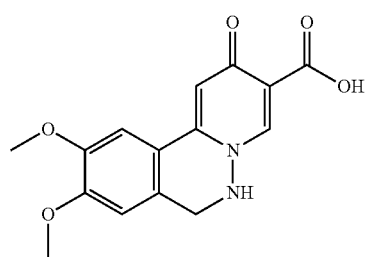 [SMILES: COc1cc2c(cc1OC)-c1cc(=O)c(C(=O)O)cn1NC2]

Step 1: Preparation of tert-butyl 2-(dimethylaminomethylene)-3-oxo-butanoate

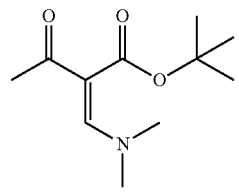

To a stirred solution of tert-butyl 3-oxobutanoate (30.0 g, 0.19 mol) in 1,4-dioxane (500 mL) was added N,N-dimethylformamide dimethyl acetal (113.0 g, 0.95 mol). The mixture was stirred at 25° C. for 16 hrs, and then concentrated under reduced pressure. The residue was diluted with H₂O (300 mL). The resulting mixture was extracted with EtOAc (200 mL) for three times. The combined organic layers were dried over anhydrous Na₂SO₄ and concentrated under reduced pressure to give crude tert-butyl 2-(dimethylaminomethylene)-3-oxo-butanoate (40.0 g) as a dark yellow liquid, which was used directly in the next step without further purification.

Step 2: Preparation of tert-butyl 4-oxopyran-3-carboxylate

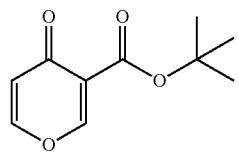

To a stirred solution of tert-butyl 2-(dimethylaminomethylene)-3-oxo-butanoate (40.0 g, 0.19 mol) and ethyl formate (27.8 g, 0.36 mol) in THF (700 mL) was added t-BuOK (52.6 g, 0.47 mol) portion wise at 0° C. Then the mixture was allowed to warm to 25° C. and stirred at the same temperature for 16 hrs. Then the reaction was quenched by adding 1 M hydrochloric acid. The resulting mixture was extracted with EtOAc (200 mL) for three times. The combined organic layers were washed with saturated NaHCO₃ aqueous solution and brine, dried over anhydrous Na₂SO₄, and concentrated under reduced pressure. The residue was purified by the flash column chromatography to give tert-butyl 4-oxopyran-3-carboxylate (9.5 g) as a dark yellow solid.

Step 3: Preparation of tert-butyl 1-ethyl-4-oxo-pyridine-3-carboxylate

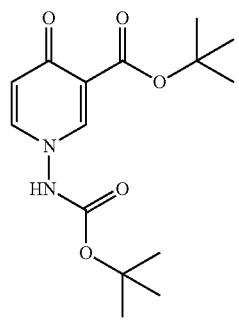 [SMILES: CC(C)(C)OC(=O)Nn1ccc(=O)c(C(=O)OC(C)(C)C)c1]

A suspension of tert-butyl N-aminocarbamate (7.0 g, 53.0 mmol) and tert-butyl 4-oxopyran-3-carboxylate (6.9 g, 35.3 mmol) in absolute EtOH (70 mL) was heated under reflux with stirring for 48 hrs. Then the mixture was cooled to rt and concentrated to give crude tert-butyl 1-ethyl-4-oxo-pyridine-3-carboxylate (1.4 g) which was used in the next step without further purification.

Step 4: Preparation of 1-bromo-2-(chloromethyl)-4,5-dimethoxy-benzene

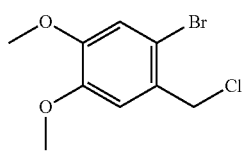

A mixture of (2-bromo-4,5-dimethoxy-phenyl)methanol (1.0 g, 4.05 mmol) and SOCl$_2$ (0.32 mL, 4.46 mmol) in DCM (10 mL) was stirred at rt for 3 hrs. The reaction mixture was then concentrated to give 1-bromo-2-(chloromethyl)-4,5-dimethoxy-benzene (1.1 g) which was used in the next step without further purification.

Step 5: Preparation of tert-butyl 1-[2-(2-bromo-4,5-dimethoxy-phenyl)-1-methyl-ethyl]-4-oxo-pyridine-3-carboxylate

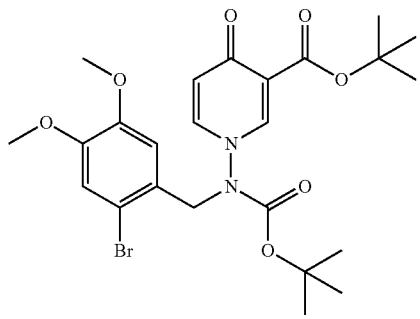 [SMILES: COc1cc(Br)c(CN(C(=O)OC(C)(C)C)n2ccc(=O)c(C(=O)OC(C)(C)C)c2)cc1OC]

A mixture of tert-butyl 1-ethyl-4-oxo-pyridine-3-carboxylate (1.4 g, 4.52 mmol), 1-bromo-2-(chloromethyl)-4,5-dimethoxy-benzene (2.4 g, 9.03 mmol) and K$_2$CO$_3$ (1.3 g, 9.03 mmol) in acetone (20 mL) was heated at 50° C. with stirring for 2 hrs. Then the mixture was cooled to rt and diluted with water (20 mL). The resulting mixture was extracted with EtOAc (50 mL) for three times. The combined organic layers were washed with brine, dried over anhydrous Na$_2$SO$_4$, and concentrated under reduced pressure to give tert-butyl 1-[2-(2-bromo-4,5-dimethoxy-phenyl)-1-methyl-ethyl]-4-oxo-pyridine-3-carboxylate (2.6 g) which was used in the next step without further purification.

Step 6: Preparation of tert-butyl 9,10-dimethoxy-2-oxo-6,7-dihydropyrido[2,1-a]phthalazine-3-carboxylate

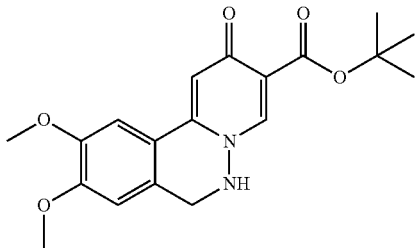 [SMILES: COc1cc2c(cc1OC)-c1cc(=O)c(C(=O)OC(C)(C)C)cn1NC2]

A mixture of tert-butyl 1-[2-(2-bromo-4,5-dimethoxy-phenyl)-1-methyl-ethyl]-4-oxo-pyridine-3-carboxylate (4.0 g, 7.42 mmol), PdBr$_2$ (99 mg, 0.37 mmol) and KOAc (1.45 g, 14.84 mmol) in DMA (15 mL) was heated at 120° C. with stirring overnight. Then the mixture was cooled to rt and filtered. The filtrate was concentrated under reduced pressure and then diluted with water (30 mL). The mixture was extracted with EtOAc (30 mL) for three times. The combined organic layers were washed with brine, dried over anhydrous Na$_2$SO$_4$, and concentrated to give crude tert-butyl 9,10-dimethoxy-2-oxo-6,7-dihydropyrido[2,1-a]phthalazine-3-carboxylate (2.0 g) which was used in the next step without further purification.

Step 7: Preparation of 9,10-dimethoxy-2-oxo-6,7-dihydropyrido[2,1-a]phthalazine-3-carboxylic acid

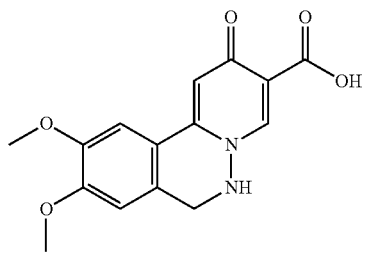 [SMILES: COc1cc2c(cc1OC)-c1cc(=O)c(C(=O)O)cn1NC2]

To a solution of tert-butyl 9,10-dimethoxy-2-oxo-6,7-dihydropyrido[2,1-a]phthalazine-3-carboxylate (100 mg, 0.28 mmol) in a mixed solvent of THF (5 mL) and H$_2$O (5 mL) was added LiOH.H$_2$O (118 mg, 2.8 mmol). The mixture was heated at 90° C. with stirring for 3 hrs. The mixture was cooled to rt and extracted with EtOAc (20 mL) for three times. The combined organic layers were washed with brine, dried over anhydrous Na$_2$SO$_4$, and concentrated under reduced pressure. The residue was purified by prep-HPLC to give 9,10-dimethoxy-2-oxo-6,7-dihydropyrido[2,1-a]phthalazine-3-carboxylic acid (10 mg) as a light yellow solid, $^1$H NMR (400 MHz, DMSO-d$_6$) δ ppm 3.87 (d, 6H) 4.09-4.34 (m, 2H), 7.05 (br. s., 1H), 7.13-7.33 (m, 1H), 7.38-7.52 (m, 1H), 7.58 (br. s., 1H), 8.26-8.53 (m, 1H); MS obsd. (ESI$^+$) [(M+H)$^+$]: 303.

Example 2: 9,10-Dimethoxy-6-methyl-2-oxo-7H-pyrido[2,1-a]phthalazine-3-carboxylic acid

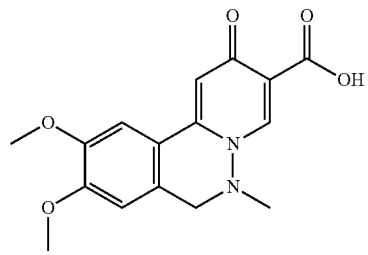 [SMILES: COc1cc2c(cc1OC)-c1cc(=O)c(C(=O)O)cn1N(C)C2]

Step 1: Preparation of tert-butyl 9,10-dimethoxy-6-methyl-2-oxo-7H-pyrido[2,1-a]phthalazine-3-carboxylate

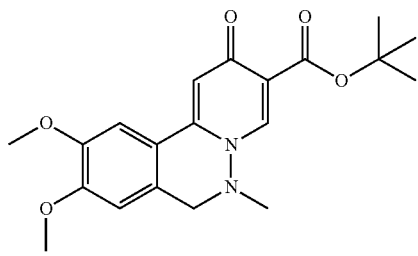 [SMILES: COc1cc2c(cc1OC)-c1cc(=O)c(C(=O)OC(C)(C)C)cn1N(C)C2]

A mixture of tert-butyl 9,10-dimethoxy-2-oxo-6,7-dihydropyrido[2,1-a]phthalazine-3-carboxylate (100 mg, 0.28 mmol), $K_2CO_3$ (77 mg, 0.56 mmol) and $CH_3I$ (174 μL, 2.8 mmol) in acetonitrile (10 mL) was heated at 90° C. with stirring for 3 hrs. The mixture was cooled down to rt and diluted with water (10 mL). The resulting mixture was extracted with EtOAc (20 mL) for three times. The combined organic layers were washed with brine, dried over anhydrous $Na_2SO_4$, and concentrated to give crude tert-butyl 9,10-dimethoxy-6-methyl-2-oxo-7H-pyrido[2,1-a]phthalazine-3-carboxylate (95 mg) which was used in the next step without further purification.

Step 2: Preparation of 9,10-dimethoxy-6-methyl-2-oxo-7H-pyrido[2,1-a]phthalazine-3-carboxylic acid

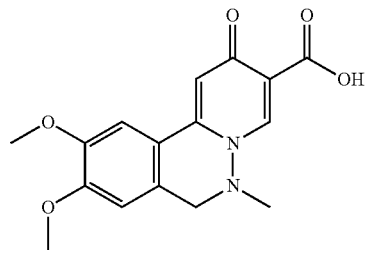 [SMILES: COc1cc2c(cc1OC)-c1cc(=O)c(C(=O)O)cn1N(C)C2]

A mixture of tert-butyl 9,10-dimethoxy-6-methyl-2-oxo-7H-pyrido[2,1-a]phthalazine-3-carboxylate (95 mg, 0.26 mmol) and $CF_3COOH$ (1 mL) in DCM (10 mL) was stirred at rt for 3 hrs. The mixture was concentrated under reduced pressure and the residue was purified by prep-HPLC to give 9,10-dimethoxy-6-methyl-2-oxo-7H-pyrido[2,1-a]phthalazine-3-carboxylic acid (10 mg) as a light yellow solid, $^1$H NMR (400 MHz, DMSO-$d_6$) δ ppm 2.65 (s, 3H) 3.81-3.94 (m, 7H) 4.33-4.43 (m, 2H) 7.00-7.11 (m, 1H) 7.50-7.57 (m, 1H) 7.60-7.66 (m, 1H) 8.57 (s, 1H); MS obsd. (ESI$^+$) [(M+H)$^+$]: 317.

Example 3: 6-Allyl-9,10-dimethoxy-2-oxo-7H-pyrido[2,1-a]phthalazine-3-carboxylic acid

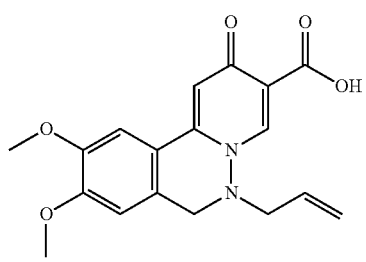 [SMILES: C=CCN1Cc2cc(OC)c(OC)cc2-c2cc(=O)c(C(=O)O)cn21]

Step 1: Preparation of tert-butyl 6-allyl-9,10-dimethoxy-2-oxo-7H-pyrido[2,1-a]phthalazine-3-carboxylate

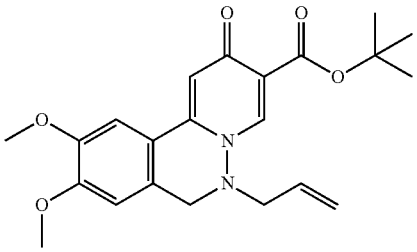 [SMILES: C=CCN1Cc2cc(OC)c(OC)cc2-c2cc(=O)c(C(=O)OC(C)(C)C)cn21]

To a solution of tert-butyl 9,10-dimethoxy-2-oxo-6,7-dihydropyrido[2,1-a]phthalazine-3-carboxylate (100 mg, 279 μmol) in DMF (3 mL) was added allyl bromide (50.6 mg, 419 μmol) and potassium carbonate (77.1 mg, 558 μmol). The resulting mixture was heated at 60° C. with stirring for 16 hrs, and then filtered. The filtrate was concentrated under reduced pressure to give tert-butyl 6-allyl-9,10-dimethoxy-2-oxo-7H-pyrido[2,1-a]phthalazine-3-carboxylate which was used in the next step without further purification.

Step 2: Preparation of 6-allyl-9,10-dimethoxy-2-oxo-7H-pyrido[2,1-a]phthalazine-3-carboxylic acid

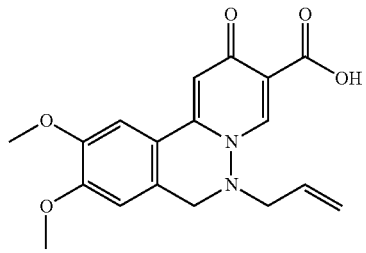 [SMILES: C=CCN1Cc2cc(OC)c(OC)cc2-c2cc(=O)c(C(=O)O)cn21]

To a solution of crude tert-butyl 6-allyl-9,10-dimethoxy-2-oxo-7H-pyrido[2,1-a]phthalazine-3-carboxylate (100 mg)

in DCM (2 mL) was added 2,2,2-trifluoroacetic acid (65 μL). The mixture was stirred for 5 hours at rt, and then concentrated under reduced pressure. The residue was purified by prep-HPLC to give 6-allyl-9,10-dimethoxy-2-oxo-7H-pyrido[2,1-a]phthalazine-3-carboxylic acid (28 mg), ¹H NMR (400 MHz, DMSO) δ ppm 8.46 (s, 1H), 7.64 (s, 1H), 7.55 (s, 1H), 7.06 (s, 1H), 6.04-5.87 (m, 1H), 5.17 (m, 1H), 5.03 (m, 1H), 4.53-4.36 (m, 2H), 3.91 (s, 3H), 3.86 (s, 3H), 3.41 (d, 2H); MS obsd. (ESI⁺) [(M+H)⁺]: 343.

Example 4: 6-Isopropyl-9,10-dimethoxy-2-oxo-7H-pyrido[2,1-a]phthalazine-3-carboxylic acid

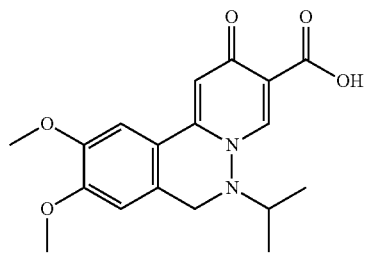 [SMILES: COc1cc2c(cc1OC)-c1cc(=O)c(C(=O)O)cn1N(C(C)C)C2]

Step 1: Preparation of tert-butyl 6-isopropyl-9,10-dimethoxy-2-oxo-7H-pyrido[2,1-a]phthalazine-3-carboxylate

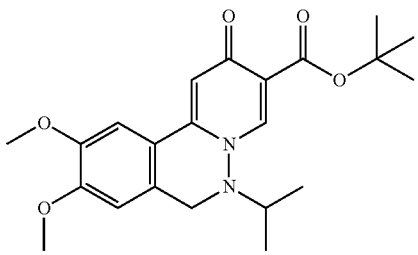 [SMILES: COc1cc2c(cc1OC)-c1cc(=O)c(C(=O)OC(C)(C)C)cn1N(C(C)C)C2]

To a solution of tert-butyl 9,10-dimethoxy-2-oxo-6,7-dihydropyrido[2,1-a]phthalazine-3-carboxylate (60 mg, 167 μmol) in DMF (2 mL) was added potassium carbonate (46.3 mg, 335 μmol) and diisopropyl sulfate (61 mg, 335 μmol). The mixture was heated at 80° C. with stirring for 14 hours, and then filtered. The filtrate was concentrated under reduced pressure to give crude tert-butyl 6-isopropyl-9,10-dimethoxy-2-oxo-7H-pyrido[2,1-a]phthalazine-3-carboxylate, which was used in the next step without further purification.

Step 2: Preparation of 6-isopropyl-9,10-dimethoxy-2-oxo-7H-pyrido[2,1-a]phthalazine-3-carboxylic acid

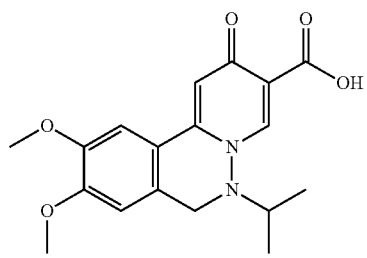 [SMILES: COc1cc2c(cc1OC)-c1cc(=O)c(C(=O)O)cn1N(C(C)C)C2]

To a solution of crude tert-butyl 6-isopropyl-9,10-dimethoxy-2-oxo-7H-pyrido[2,1-a]phthalazine-3-carboxylate (62 mg) in DCM (5 mL) was added TFA (62 μL). The mixture was stirred for 3 hours at rt, and then concentrated under reduced pressure. The residue was purified by prep-HPLC to give 6-isopropyl-9,10-dimethoxy-2-oxo-7H-pyrido[2,1-a]phthalazine-3-carboxylic acid (4 mg), ¹H NMR (400 MHz, DMSO) δ ppm 8.16 (s, 1H), 7.81 (s, 1H), 7.73 (s, 1H), 7.13 (s, 1H), 4.37-4.28 (m, 2H), 3.94 (s, 3H), 3.89 (s, 3H), 2.53-2.51 (m, 1H), 1.39 (d, 6H); MS obsd. (ESI⁺) [(M+H)⁺]: 345.

Example 5: 6-Isobutyl-9,10-dimethoxy-2-oxo-7H-pyrido[2,1-a]phthalazine-3-carboxylic acid

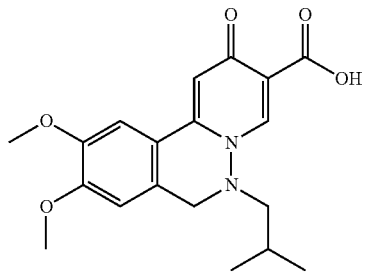 [SMILES: COc1cc2c(cc1OC)-c1cc(=O)c(C(=O)O)cn1N(CC(C)C)C2]

Step 1: Preparation of tert-butyl 9,10-dimethoxy-6-(2-methylallyl)-2-oxo-7H-pyrido[2,1-a]phthalazine-3-carboxylate

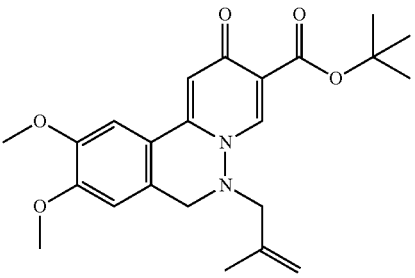 [SMILES: C=C(C)CN1Cc2cc(OC)c(OC)cc2-c2cc(=O)c(C(=O)OC(C)(C)C)cn21]

To a solution of tert-butyl 9,10-dimethoxy-2-oxo-6,7-dihydropyrido[2,1-a]phthalazine-3-carboxylate (100 mg, 279 μmol) in DMF (3 mL) was added 3-bromo-2-methylprop-1-ene (75.3 mg, 558 μmol) and potassium carbonate (77.1 mg, 558 μmol). The mixture was heated at 60° C. with stirring for 16 hours, and then filtered. The filtrate was concentrated under reduced pressure to give crude tert-butyl 9,10-dimethoxy-6-(2-methylallyl)-2-oxo-7H-pyrido[2,1-a]phthalazine-3-carboxylate (130 mg) which was used in the next step without further purification.

Step 2: Preparation of 9,10-dimethoxy-6-(2-methylallyl)-2-oxo-7H-pyrido[2,1-a]phthalazine-3-carboxylic acid

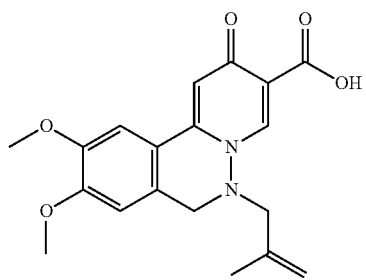 [SMILES: C=C(C)CN1Cc2cc(OC)c(OC)cc2-c2cc(=O)c(C(=O)O)cn21]

To a solution of crude tert-butyl 9,10-dimethoxy-6-(2-methylallyl)-2-oxo-7H-pyrido[2,1-a]phthalazine-3-carboxylate (130 mg, 268 μmol) in DCM (2 mL) was added TFA (99.2 μL). The mixture was stirred at rt for 5 hours, and then concentrated under reduced pressure. The residue was purified by column chromatography to give 9,10-dimethoxy-6-(2-methylallyl)-2-oxo-7H-pyrido[2,1-a]phthalazine-3-carboxylic acid (30 mg).

Step 3: Preparation of 6-isobutyl-9,10-dimethoxy-2-oxo-7H-pyrido[2,1-a]phthalazine-3-carboxylic acid

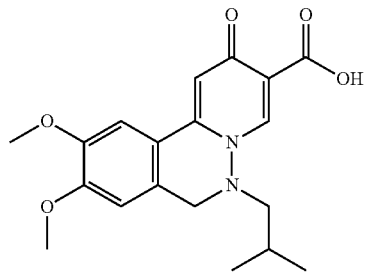 [SMILES: COc1cc2c(cc1OC)-c1cc(=O)c(C(=O)O)cn1N(CC(C)C)C2]

To a solution of 9,10-dimethoxy-6-(2-methylallyl)-2-oxo-7H-pyrido[2,1-a]phthalazine-3-carboxylic acid (30 mg, 84.2 μmol) in EtOH (3 mL) was added Pd/C (6 mg). The mixture was stirred under an atmosphere of hydrogen at rt for 16 hours. The mixture was filtered and the filtrate was concentrated under reduced pressure to give 6-isobutyl-9,10-dimethoxy-2-oxo-6,7-dihydro-2H-pyrido[2,1-a]phthalazine-3-carboxylic acid (13 mg), $^1$H NMR (400 MHz, DMSO) δ ppm 8.40 (s, 1H), 7.62 (s, 1H), 7.55 (s, 1H), 7.09 (s, 1H), 4.42 (m, 2H), 3.90 (s, 3H), 3.86 (s, 3H), 2.55 (d, 2H), 1.69-1.56 (m, 1H), 0.91 (d, 6H); MS obsd. (ESI$^+$) [(M+H)$^+$]: 359.

Example 6: 6-Isobutyl-10-methoxy-9-(3-methoxypropoxy)-2-oxo-7H-pyrido[2,1-a]phthalazine-3-carboxylic acid

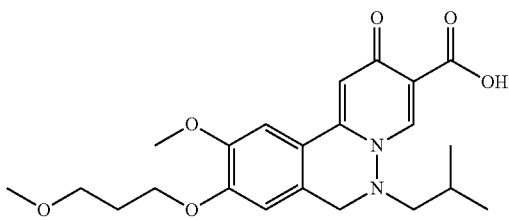 [SMILES: COCCCOc1cc2c(cc1OC)-c1cc(=O)c(C(=O)O)cn1N(CC(C)C)C2]

Step 1: Preparation of 5-benzyloxy-2-bromo-4-methoxy-benzaldehyde

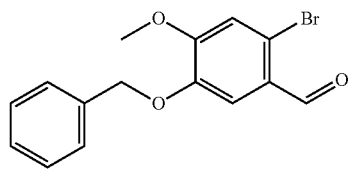 [SMILES: COc1cc(Br)c(C=O)cc1OCc1ccccc1]

To a solution of 2-bromo-5-hydroxy-4-methoxy-benzaldehyde (25 g, 108 mmol) in MeCN (500 mL) was added (chloromethyl)benzene (13.7 g, 108 mmol) and potassium carbonate (29.9 g, 216 mmol). The mixture was heated at 80° C. with stirring for 15 hours. After being cooled to rt, the mixture was filtered. The filtrate was concentrated under reduced pressure. The residue was partitioned between brine and DCM. The organic layer was dried over anhydrous Na$_2$SO$_4$ and concentrated under reduced pressure to give 5-(benzyloxy)-2-bromo-4-methoxy-benzaldehyde (34.2 g, 96.9 mmol) which was used in the next step without further purification.

Step 2: Preparation of (5-benzyloxy-2-bromo-4-methoxy-phenyl)methanol

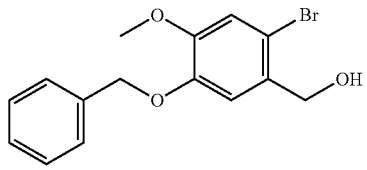 [SMILES: COc1cc(Br)c(CO)cc1OCc1ccccc1]

To a solution of 5-(benzyloxy)-2-bromo-4-methoxy-benzaldehyde (35 g, 106 mmol) in MeOH (600 mL) was added NaBH$_4$ (4 g, 106 mmol) portion-wise at 0° C. The reaction mixture was allowed to warm to rt, stirred at rt for three hours, and then quenched with water. The mixture was concentrated under reduced pressure. The residue was partitioned between brine and DCM. The organic layer was dried over anhydrous Na$_2$SO$_4$ and concentrated under reduced pressure to give (5-(benzyloxy)-2-bromo-4-methoxy-phenyl)methanol (32.5 g, 100 mmol), which was used in the next step without further purification.

Step 3: Preparation of 1-benzyloxy-4-bromo-5-(chloromethyl)-2-methoxy-benzene

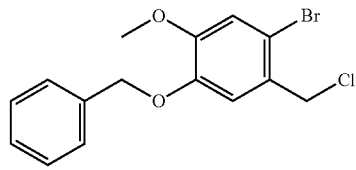 [SMILES: COc1cc(Br)c(CCl)cc1OCc1ccccc1]

To a solution of (5-(benzyloxy)-2-bromo-4-methoxy-phenyl)methanol (5 g, 14.7 mmol) in DCM (50 mL) was added SOCl$_2$ (1.61 mL, 22 mmol) drop-wise at rt. The mixture was stirred at rt for two hours, and then concentrated under reduced pressure to give 1-(benzyloxy)-4-bromo-5-(chloromethyl)-2-methoxy-benzene (5 g, 13.8 mmol, 93.6% yield), which was used in the next step without further purification.

Step 4: Preparation of tert-butyl 1-[(5-benzyloxy-2-bromo-4-methoxy-phenyl)methyl-tert-butoxycarbonyl-amino]-4-oxo-pyridine-3-carboxylate

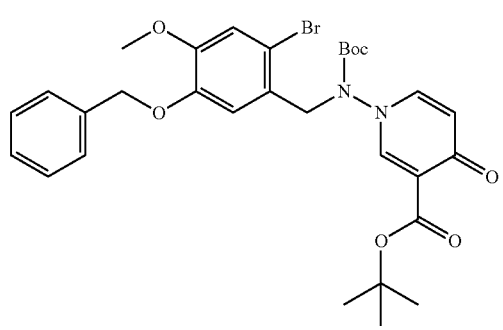 [SMILES: COc1cc(Br)c(CN(C(=O)OC(C)(C)C)n2ccc(=O)c(C(=O)OC(C)(C)C)c2)cc1OCc1ccccc1]

To a solution of 1-(benzyloxy)-4-bromo-5-(chloromethyl)-2-methoxy-benzene (5.0 g, 14.6 mmol) in MeCN (100 mL) was added potassium carbonate (4.05 g, 29.3 mmol) and tert-butyl 1-((tert-butoxycarbonyl)amino)-4-oxo-1,4-dihydropyridine-3-carboxylate (14 g, 29.3 mmol). The mixture was heated at 80° C. with stirring for 5 hours. After being cooled to rt, the mixture was filtered. The filtrate was concentrated under reduced pressure, and the residue was purified by column chromatography to give tert-butyl 1-[(5-benzyloxy-2-bromo-4-methoxy-phenyl)methyl-tert-butoxycarbonyl-amino]-4-oxo-pyridine-3-carboxylate (5.3 g, 7.75 mmol).

Step 5: Preparation of tert-butyl 9-benzyloxy-10-methoxy-2-oxo-6,7-dihydropyrido[2,1-a]phthalazine-3-carboxylate and di-tert-butyl 9-benzyloxy-10-methoxy-2-oxo-7H-pyrido[2,1-a]phthalazine-3,6-dicarboxylate

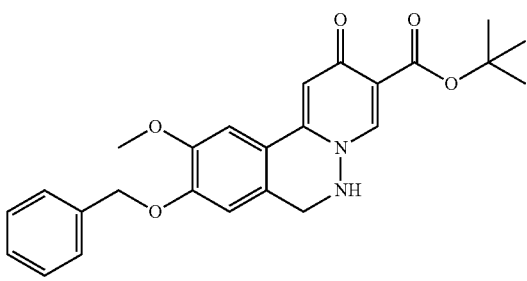

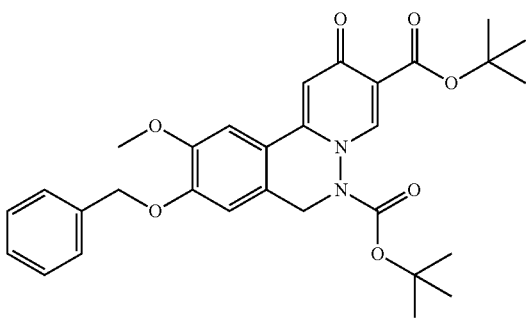

To a 15 mL microwave vial was added tert-butyl 1-[(5-benzyloxy-2-bromo-4-methoxy-phenyl)methyl-tert-butoxycarbonyl-amino]-4-oxo-pyridine-3-carboxylate (700 mg, 1.14 mmol), palladium (II) bromide (90.8 mg, 341 µmol), potassium acetate (223 mg, 2.27 mmol) and DMF (5 mL). The vial was capped and heated under microwave at 100° C. for 5 hours. The mixture was filtered and the filtrate was concentrated under reduced pressure to give a mixture of tert-butyl 9-benzyloxy-10-methoxy-2-oxo-6,7-dihydropyrido[2,1-a]phthalazine-3-carboxylate and di-tert-butyl 9-benzyloxy-10-methoxy-2-oxo-7H-pyrido[2,1-a]phthalazine-3,6-dicarboxylate, which was used in the next step without further purification.

Step 6: Preparation of 9-benzyloxy-10-methoxy-2-oxo-6,7-dihydropyrido[2,1-a]phthalazine-3-carboxylic acid

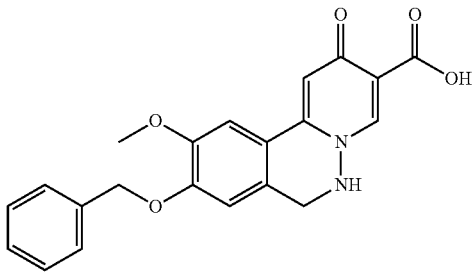 [SMILES: COc1cc2c(cc1OCc1ccccc1)CNn1cc(C(=O)O)c(=O)cc1-2]

To a solution of the crude mixture of tert-butyl 9-benzyloxy-10-methoxy-2-oxo-6,7-dihydropyrido[2,1-a]phthalazine-3-carboxylate and di-tert-butyl 9-benzyloxy-10-methoxy-2-oxo-7H-pyrido[2,1-a]phthalazine-3,6-dicarboxylate (4.0 g) in DCM (20 mL) was added TFA (20 mL). The mixture was stirred at rt for 15 hours, and then concentrated under reduced pressure. The residue was treated with a mixture solvent of petroleum ether/ethyl acetate (10:1, V/V). The mixture was filtered and the filter cake was dried under reduced pressure to give 9-benzyloxy-10-methoxy-2-oxo-6,7-dihydropyrido[2,1-a]phthalazine-3-carboxylic acid (2.0 g).

Step 7: Preparation of methyl 9-benzyloxy-10-methoxy-2-oxo-6,7-dihydropyrido[2,1-a]phthalazine-3-carboxylate

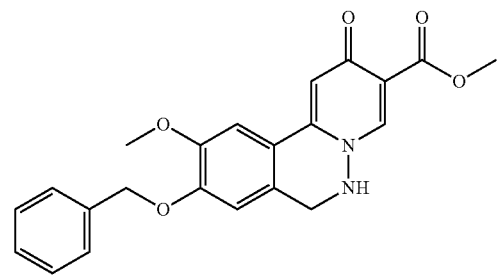 [SMILES: COC(=O)c1cn2c(cc1=O)-c1cc(OC)c(OCc3ccccc3)cc1CN2]

To a suspension of 9-benzyloxy-10-methoxy-2-oxo-6,7-dihydropyrido[2,1-a]phthalazine-3-carboxylic acid (0.70 g, 1.85 mmol) in MeOH (20 mL) was added catalytic amount of concentrated sulfuric acid (50 µL). The mixture was heated at 80° C. for 20 hours. The mixture was concentrated under reduced pressure, and the residue was neutralized with saturated aqueous NaHCO$_3$. The resulting mixture was extracted with DCM. The organic layer was dried over anhydrous Na$_2$SO$_4$ and concentrated under reduced pressure to give methyl 9-benzyloxy-10-methoxy-2-oxo-6,7-dihydropyrido[2,1-a]phthalazine-3-carboxylate (703 mg, 1.79 mmol).

Step 8: Preparation of 9-benzyloxy-10-methoxy-6-(2-methylallyl)-2-oxo-7H-pyrido[2,1-a]phthalazine-3-carboxylic acid

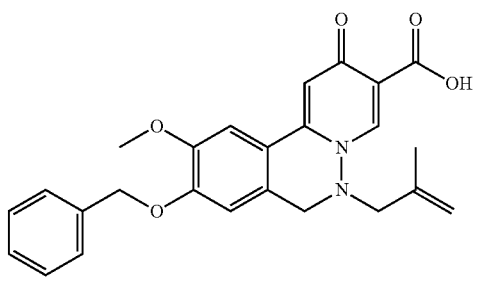 [SMILES: C=C(C)CN1Cc2cc(OCc3ccccc3)c(OC)cc2-c2cc(=O)c(C(=O)O)cn21]

To a solution of methyl 9-benzyloxy-10-methoxy-2-oxo-6,7-dihydropyrido[2,1-a]phthalazine-3-carboxylate (0.20 g, 510 μmol) in DMF (20 mL) was added sodium hydride (61.2 mg, 1.53 mmol) at 0° C. The mixture was stirred for 30 minutes, and then 3-bromo-2-methylprop-1-ene (275 mg, 2.04 mmol) was added. The resulting mixture was allowed to warm to rt and stirred at rt for 40 hours. To the mixture was added water and sodium hydroxide (40.8 mg, 1.02 mmol). The resulting mixture was stirred for additional two hours, and then acidified with 6 M hydrochloric acid, and extracted with DCM. The organic layer was dried over anhydrous $Na_2SO_4$ and concentrated under reduced pressure to give crude 9-benzyloxy-10-methoxy-6-(2-methylallyl)-2-oxo-7H-pyrido[2,1-a]phthalazine-3-carboxylic acid (241 mg), which was used in the next step without further purification.

Step 9: Preparation of 9-hydroxy-6-isobutyl-10-methoxy-2-oxo-7H-pyrido[2,1-a]phthalazine-3-carboxylic acid

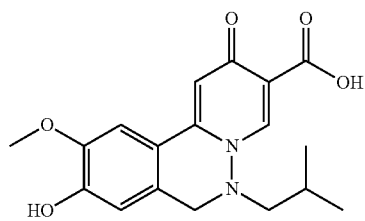 [SMILES: COc1cc2c(cc1O)CN(CC(C)C)n1cc(C(=O)O)c(=O)cc1-2]

To a solution of crude 9-benzyloxy-10-methoxy-6-(2-methylallyl)-2-oxo-7H-pyrido[2,1-a]phthalazine-3-carboxylic acid (241 mg) in EtOH (15 mL) was added Pd/C (50 mg). The mixture was stirred under hydrogen atmosphere at rt for 16 hours. Then the mixture was filtered and the filtrate was concentrated under reduced pressure to give crude 9-hydroxy-6-isobutyl-10-methoxy-2-oxo-7H-pyrido[2,1-a]phthalazine-3-carboxylic acid (123 mg), which was used in the next step without further purification.

Step 10: Preparation 6-isobutyl-10-methoxy-9-(3-methoxypropoxy)-2-oxo-7H-pyrido[2,1-a]phthalazine-3-carboxylic acid

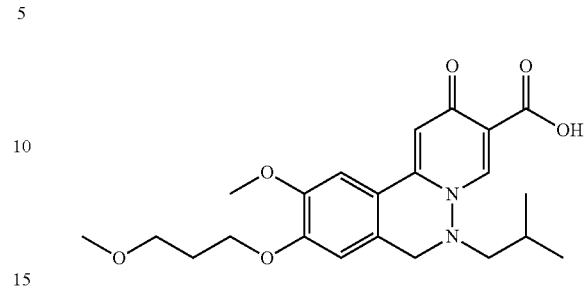

To a solution of crude 9-hydroxy-6-isobutyl-10-methoxy-2-oxo-7H-pyrido[2,1-a]phthalazine-3-carboxylic acid (60 mg) in DMF (3 mL) was added potassium carbonate (74.2 mg, 537 μmol) and 1-bromo-3-methoxypropane (61.6 mg, 402 μmol). The mixture was heated at 100° C. with stirring for three hours, and then cooled to rt. To the mixture was added water (3 mL) and sodium hydroxide (10.7 mg, 268 μmol). The resulting mixture was stirred at rt for two hours, then acidified with 6 M hydrochloric acid and extracted with DCM. The organic layer was concentrated under reduced pressure, and the residue was purified by prep-HPLC to give 6-isobutyl-10-methoxy-9-(3-methoxypropoxy)-2-oxo-7H-pyrido[2,1-a]phthalazine-3-carboxylic acid (17 mg), $^1$H NMR (400 MHz, DMSO-$d_6$) δ ppm 8.40 (s, 1H), 7.62 (s, 1H), 7.55 (s, 1H), 7.10 (s, 1H), 4.46-4.36 (m, 2H), 4.11 (t, 2H), 3.90 (s, 3H), 3.48 (t, 2H), 3.26 (s, 3H), 2.55 (d, 2H), 2.05-1.95 (m, 2H), 1.69-1.57 (m, 1H), 0.91 (d, 6H); MS obsd. (ESI$^+$) [(M+H)$^+$]: 417.

Example 7: 6-Isobutyl-10-methoxy-2-oxo-9-(2,2,2-trifluoroethoxy)-7H-pyrido[2,1-a]phthalazine-3-carboxylic acid

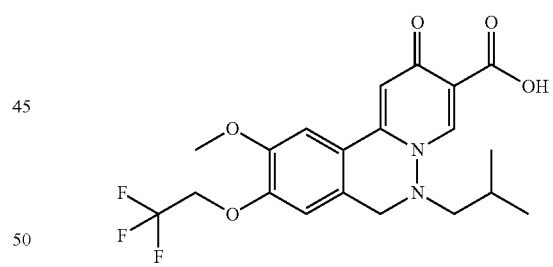

To a solution of crude 9-hydroxy-6-isobutyl-10-methoxy-2-oxo-7H-pyrido[2,1-a]phthalazine-3-carboxylic acid (60 mg) in DMF (3 mL) was added potassium carbonate (74.2 mg, 537 μmol) and 1,1,1-trifluoro-2-iodoethane (169 mg, 805 μmol). The mixture was heated at 100° C. with stirring for 20 hours. After being cooled to rt, the reaction mixture was partitioned between 1 M hydrochloric acid and DCM. The organic layer was concentrated under reduced pressure, and the residue was purified by prep-HPLC to give 6-isobutyl-10-methoxy-2-oxo-9-(2,2,2-trifluoroethoxy)-7H-pyrido[2,1-a]phthalazine-3-carboxylic acid (7 mg), $^1$H NMR (400 MHz, DMSO-$d_6$) δ ppm 8.42 (s, 1H), 7.72 (s, 1H), 7.62 (s, 1H), 7.22 (s, 1H), 4.90-4.78 (m, 2H), 4.48-4.35 (m, 2H), 3.94 (s, 3H), 2.54 (d, 2H), 1.66-1.56 (m, 1H), 0.91 (d, 6H); MS obsd. (ESI$^+$) [(M+H)+]: 427.

Example 8: 6-Isobutyl-10-methoxy-2-oxo-9-(tetrahydropyran-4-ylmethoxy)-7H-pyrido[2,1-a]phthalazine-3-carboxylic acid

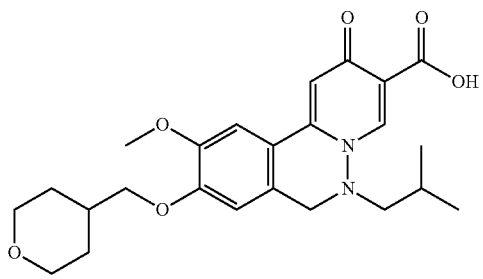 [SMILES: COc1cc2c(cc1OCC1CCOCC1)CN(CC(C)C)n1cc(C(=O)O)c(=O)cc1-2]

To a solution of crude 9-hydroxy-6-isobutyl-10-methoxy-2-oxo-7H-pyrido[2,1-a]phthalazine-3-carboxylic acid (60 mg) in DMF (3 mL) was added potassium carbonate (74.2 mg, 537 μmol) and 4-(iodomethyl)tetrahydro-2H-pyran (91 mg, 402 μmol). The mixture was heated at 100° C. with stirring for 3 hrs, and then cooled to rt. To the above mixture was added water (3 mL) and sodium hydroxide (10.7 mg, 268 μmol). The resulting mixture was stirred at rt for 2 hrs, and then acidified with 6 M hydrochloric acid. The mixture was partitioned between brine and DCM. The organic layer was separated and concentrated under reduced pressure. The residue was purified by prep-HPLC to give 6-isobutyl-10-methoxy-2-oxo-9-(tetrahydropyran-4-ylmethoxy)-7H-pyrido[2,1-a]phthalazine-3-carboxylic acid (5 mg), $^1$H NMR (400 MHz, CDCl$_3$) δ ppm 8.60 (s, 1H), 7.20 (s, 1H), 7.04 (s, 1H), 6.72 (s, 1H), 4.36-4.16 (m, 2H), 4.08-4.01 (m, 2H), 3.94 (s, 3H), 3.92 (d, 2H), 3.52-3.43 (m, 2H), 2.53 (d, 2H), 2.24-2.19 (m, 1H), 2.05-1.99 (m, 1H), 1.69-1.60 (m, 2H), 1.54-1.42 (m, 2H), 0.96 (d, 6H). MS obsd. (ESI$^+$) [(M+H)$^+$]: 443.

Example 9: 6-Isobutyl-10-methoxy-9-(3-methylsulfonylpropoxy)-2-oxo-7H-pyrido[2,1-a]phthalazine-3-carboxylic acid

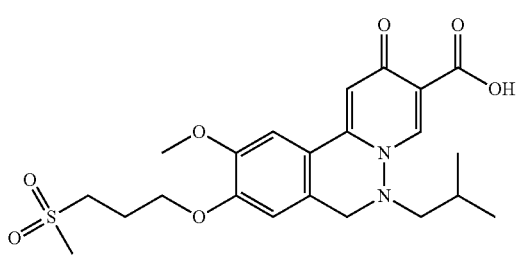 [SMILES: COc1cc2c(cc1OCCCS(C)(=O)=O)CN(CC(C)C)n1cc(C(=O)O)c(=O)cc1-2]

To a solution of crude 9-hydroxy-6-isobutyl-10-methoxy-2-oxo-7H-pyrido[2,1-a]phthalazine-3-carboxylic acid (60 mg) in DMF (3 mL) was added potassium carbonate (74.2 mg, 537 μmol) and 3-(methylsulfonyl)propyl 4-methylbenzenesulfonate (118 mg, 402 μmol). The mixture was heated at 100° C. with stirring for 3 hrs, and then cooled to rt. To the above mixture was added water (3 mL) and sodium hydroxide (10.7 mg, 268 μmol). The resulting mixture was stirred at rt for 2 hrs, and then acidified with 6 M hydrochloric acid. The mixture was partitioned between brine and DCM. The organic layer was separated and concentrated under reduced pressure. The residue was purified by prep-HPLC to give 6-isobutyl-10-methoxy-9-(3-methylsulfonylpropoxy)-2-oxo-7H-pyrido[2,1-a]phthalazine-3-carboxylic acid (7.8 mg), $^1$H NMR (400 MHz, DMSO-d$_6$) δ ppm 8.40 (s, 1H), 7.64 (s, 1H), 7.55 (s, 1H), 7.09 (s, 1H), 4.44-4.38 (m, 2H), 4.22-4.15 (m, 2H), 3.91 (s, 3H), 3.27-3.22 (m, 2H), 3.04 (s, 3H), 2.54 (d, 2H), 2.23-2.16 (m, 2H), 1.66-1.56 (m, 1H), 0.91 (d, 6H); MS obsd. (ESI$^+$) [(M+H)$^+$]: 465.

Example 10: 6-Isobutyl-10-methoxy-9-(2-morpholinoethoxy)-2-oxo-7H-pyrido[2,1-a]phthalazine-3-carboxylic acid

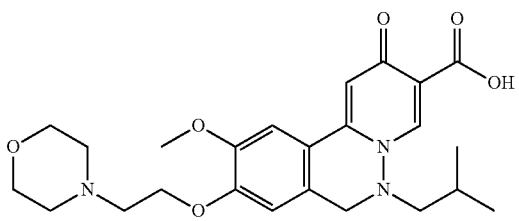 [SMILES: COc1cc2c(cc1OCCN1CCOCC1)CN(CC(C)C)n1cc(C(=O)O)c(=O)cc1-2]

To a solution of crude 9-hydroxy-6-isobutyl-10-methoxy-2-oxo-7H-pyrido[2,1-a]phthalazine-3-carboxylic acid (57 mg) in DMF (3 mL) was added potassium carbonate (88.1 mg, 637 μmol) and 4-(2-bromoethyl)morpholine hydrobromide (87.6 mg, 319 μmol) The mixture was heated at 100° C. with stirring for 3 hrs, and then cooled to rt. To the above mixture was added water (3 mL) and sodium hydroxide (10.2 mg, 255 μmol). The resulting mixture was stirred at rt for 2 hrs, and then acidified with 6 M hydrochloric acid. The mixture was partitioned between brine and DCM. The organic layer was separated and concentrated under reduced pressure. The residue was purified by prep-HPLC to give 6-isobutyl-10-methoxy-9-(2-morpholinoethoxy)-2-oxo-7H-pyrido[2,1-a]phthalazine-3-carboxylic acid (10 mg), $^1$H NMR (400 MHz, CDCl$_3$) δ ppm 8.60 (s, 1H), 7.21 (s, 1H), 7.05 (s, 1H), 6.75 (s, 1H), 4.30-4.23 (m, 4H), 3.95 (s, 3H), 3.76-3.73 (m, 4H), 2.93-2.89 (m, 2H), 2.65-2.62 (m, 4H), 2.53 (d, 2H), 1.68-1.61 (m, 1H), 0.97 (d, 6H); MS obsd. (ESI$^+$) [(M+H)$^+$]: 458.

Example 11: 9-(3-Hydroxy-2,2-dimethyl-propoxy)-6-isobutyl-10-methoxy-2-oxo-7H-pyrido[2,1-a]phthalazine-3-carboxylic acid

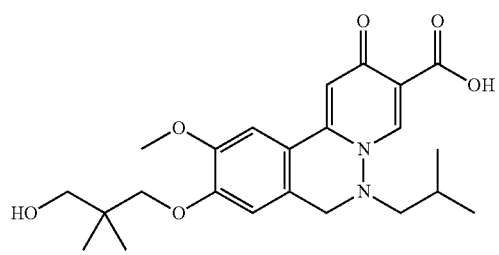 [SMILES: COc1cc2c(cc1OCC(C)(C)CO)CN(CC(C)C)n1cc(C(=O)O)c(=O)cc1-2]

To a solution of crude 9-hydroxy-6-isobutyl-10-methoxy-2-oxo-7H-pyrido[2,1-a]phthalazine-3-carboxylic acid (57 mg, 127 μmol) in DMF (3 mL) was added potassium carbonate (88.1 mg, 637 μmol) and 3-bromo-2,2-dimethyl-propan-1-ol (85.2 mg, 510 μmol). The mixture was heated at 100° C. with stirring for 3 hrs, and then cooled to rt. To the above mixture was added water (3 mL) and sodium hydroxide (10.2 mg, 255 μmol). The resulting mixture was stirred at rt for 2 hrs, and then acidified with 6 M hydrochloric acid. The mixture was partitioned between brine and DCM. The organic layer was separated and concentrated under reduced pressure. The residue was purified by prep-HPLC to give 9-(3-hydroxy-2,2-dimethyl-propoxy)-6-isobutyl-10-methoxy-2-oxo-7H-pyrido[2,1-a]phthalazine-3-carboxylic acid (7 mg), $^1$H NMR (400 MHz, DMSO-$d_6$) δ ppm 8.39 (s, 1H), 7.61 (s, 1H), 7.52 (s, 1H), 7.09 (s, 1H), 4.67-4.61 (m, 1H), 4.42-4.37 (m, 2H), 3.90 (s, 3H), 3.78 (s, 2H), 3.30-3.28 (m, 2H), 2.54 (d, 2H), 1.65-1.58 (m, 1H), 0.95 (s, 6H), 0.90 (d, 6H); MS obsd. (ESI$^+$) [(M+H)$^+$]: 431.

Example 12: 9-(4-Carboxybutoxy)-6-isobutyl-10-methoxy-2-oxo-7H-pyrido[2,1-a]phthalazine-3-carboxylic acid

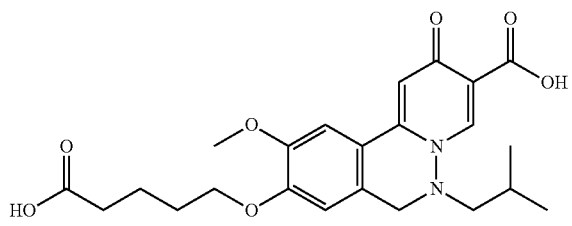 [SMILES: COc1cc2c(cc1OCCCCC(=O)O)CN(CC(C)C)n1cc(C(=O)O)c(=O)cc1-2]

To a solution of crude 9-hydroxy-6-isobutyl-10-methoxy-2-oxo-7H-pyrido[2,1-a]phthalazine-3-carboxylic acid (57 mg, 127 μmol) in DMF (3 mL) was added potassium carbonate (88.1 mg, 637 μmol) and methyl 5-bromopentanoate (74.6 mg, 382 μmol). The mixture was heated at 100° C. with stirring for 3 hrs, and then cooled to rt. To the above mixture was added water (3 mL) and sodium hydroxide (20.4 mg, 510 μmol). The resulting mixture was stirred at rt for 2 hrs, and then acidified with 6 M hydrochloric acid. The mixture was partitioned between brine and DCM. The organic layer was separated and concentrated under reduced pressure. The residue was purified by prep-HPLC to give 9-(4-carboxybutoxy)-6-isobutyl-10-methoxy-2-oxo-7H-pyrido[2,1-a]phthalazine-3-carboxylic acid (7 mg), $^1$H NMR (400 MHz, DMSO-$d_6$) δ ppm 8.39 (s, 1H), 7.61 (s, 1H), 7.53 (s, 1H), 7.08 (s, 1H), 4.44-4.36 (m, 2H), 4.09-4.03 (m, 2H), 3.90 (s, 3H), 2.53 (d, 2H), 2.33-2.26 (m, 2H), 1.81-1.73 (m, 2H), 1.69-1.59 (m, 3H), 0.91 (d, 6H). MS obsd. (ESI$^+$) [(M+H)$^+$]: 445.

Example 13: 9-(3-Cyanopropoxy)-6-isobutyl-10-methoxy-2-oxo-7H-pyrido[2,1-a]phthalazine-3-carboxylic acid

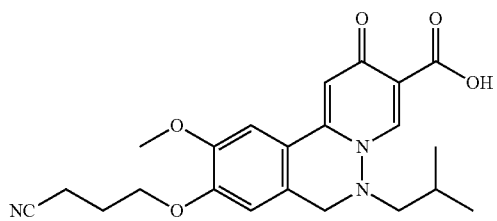 [SMILES: COc1cc2c(cc1OCCCC#N)CN(CC(C)C)n1cc(C(=O)O)c(=O)cc1-2]

To a solution of crude 9-hydroxy-6-isobutyl-10-methoxy-2-oxo-7H-pyrido[2,1-a]phthalazine-3-carboxylic acid (57 mg, 127 μmol) in DMF (3 mL) was added potassium carbonate (88.1 mg, 637 μmol) and 4-bromobutanenitrile (56.6 mg, 382 μmol). The mixture was heated at 100° C. with stirring for 3 hrs, and then cooled to rt. To the above mixture was added water (3 mL) and sodium hydroxide (10.2 mg, 255 μmol). The resulting mixture was stirred at rt for 2 hrs, and then acidified with 6 M hydrochloric acid. The mixture was partitioned between brine and DCM. The organic layer was separated and concentrated under reduced pressure. The residue was purified by prep-HPLC to give 9-(3-cyanopropoxy)-6-isobutyl-10-methoxy-2-oxo-7H-pyrido[2,1-a]phthalazine-3-carboxylic acid (10 mg), $^1$H NMR (400 MHz, DMSO-$d_6$) δ ppm 8.40 (s, 1H), 7.63 (s, 1H), 7.55 (s, 1H), 7.12 (s, 1H), 4.45-4.36 (m, 2H), 4.16-4.09 (m, 2H), 3.90 (s, 3H), 2.70-2.62 (m, 2H), 2.54 (d, 2H), 2.09-2.05 (m, 2H), 1.66-1.57 (m, 1H), 0.91 (d, 6H). MS obsd. (ESI$^+$) [(M+H)$^+$]: 412.

Example 14: 9-[5-(Tert-butoxycarbonylamino)pentoxy]-6-isobutyl-10-methoxy-2-oxo-7H-pyrido[2,1-a]phthalazine-3-carboxylic acid

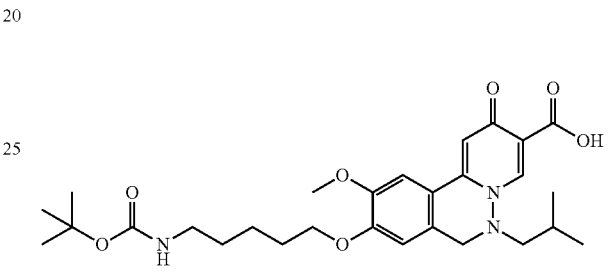

To a solution of crude 9-hydroxy-6-isobutyl-10-methoxy-2-oxo-7H-pyrido[2,1-a]phthalazine-3-carboxylic acid (57 mg, 127 μmol) in DMF (3 mL) was added potassium carbonate (88.1 mg, 637 μmol) and 5-((tert-butoxycarbonyl)amino)pentyl 4-methylbenzenesulfonate (137 mg, 382 μmol). The mixture was heated at 100° C. with stirring for 3 hrs, and then cooled to rt. To the above mixture was added water (3 mL) and sodium hydroxide (10.2 mg, 255 μmol). The resulting mixture was stirred at rt for 2 hrs, and then acidified with 6 M hydrochloric acid. The mixture was partitioned between brine and DCM. The organic layer was separated and concentrated under reduced pressure. The residue was purified by prep-HPLC to give 9-[5-(tert-butoxycarbonylamino)pentoxy]-6-isobutyl-10-methoxy-2-oxo-7H-pyrido[2,1-a]phthalazine-3-carboxylic acid (13 mg), $^1$H NMR (400 MHz, DMSO-$d_6$) δ ppm 8.39 (s, 1H), 7.61 (s, 1H), 7.53 (s, 1H), 7.08 (s, 1H), 6.83-6.77 (m, 1H), 4.43-4.36 (m, 2H), 4.07-4.00 (m, 2H), 3.89 (s, 3H), 2.97-2.89 (m, 2H), 2.54 (d, 2H), 1.79-1.71 (m, 2H), 1.66-1.56 (m, 1H), 1.46-1.34 (m, 13H), 0.90 (d, 6H). MS obsd. (ESI$^+$) [(M+H)$^+$]: 530.

Example 15: 9-(5-Aminopentoxy)-6-isobutyl-10-methoxy-2-oxo-7H-pyrido[2,1-a]phthalazine-3-carboxylic acid hydrochloride

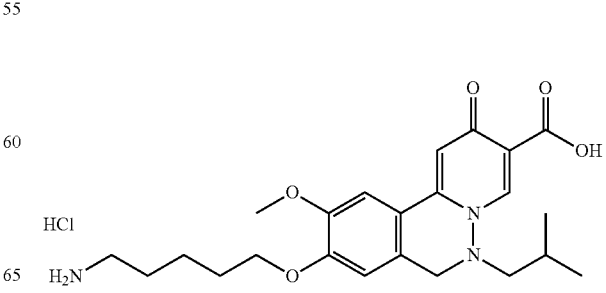

To a solution of 9-[5-(tert-butoxycarbonylamino)pentoxy]-6-isobutyl-10-methoxy-2-oxo-7H-pyrido[2,1-a]phthalazine-3-carboxylic acid (8 mg, 15.1 μmol) in MeCN (0.5 mL) was added hydrochloric acid (5.51 μL, 181 μmol). The mixture was stirred at rt for 2 hrs, and then concentrated under reduced pressure to 9-(5-aminopentoxy)-6-isobutyl-10-methoxy-2-oxo-7H-pyrido[2,1-a]phthalazine-3-carboxylic acid hydrochloride (7 mg), $^1$H NMR (400 MHz, DMSO-$d_6$) δ ppm 8.40 (s, 1H), 7.90-7.79 (m, 3H), 7.61 (s, 1H), 7.54 (s, 1H), 7.09 (s, 1H), 4.45-4.36 (m, 2H), 4.09-4.02 (m, 2H), 3.90 (s, 3H), 2.85-2.76 (m, 2H), 2.56-2.52 (m, 2H), 1.83-1.77 (m, 2H), 1.67-1.58 (m, 3H), 1.52-1.42 (m, 2H), 0.91 (d, 6H); MS obsd. (ESI$^+$) [(M+H)$^+$]: 430.

Biological Examples

Example 16 Materials and Methods

HBV Cell Line

HepG2.2.15 cells (Acs et al. *Proc Natl Acad Sci* USA, 84, (1987), 4641-4), a constitutively HBV-expressing cell line were cultured in DMEM+Glutamax-I medium (Invitrogen, Carlsbad, Calif., USA), supplemented with 10% fetal bovine serum (Invitrogen) and G418 (Invitrogen) at a final concentration of 200 mg/L and maintained in 5% $CO_2$ at 37° C.

HBsAg Assay

HepG2.2.15 cells were seeded in duplicate into white, 96-well plates at 1.5×10$^4$ cells/well. The cells were treated with a three-fold serial dilution series of the compounds in DMSO. The final DMSO concentration in all wells was 1% and DMSO was used as no drug control.

The HBsAg chemiluminescence immunoassay (CLIA) kit (Autobio Diagnostics Co., Zhengzhou, China, Catalog number: CL0310-2) was used to measure the levels of secreted HBV antigens semi-quantitatively. For the detection 50 μL/well culture supernatant was used and HBsAg was quantified using HBsAg chemiluminescence immunoassay (CLIA) kit (Autobio Diagnostics Co., Zhengzhou, China, Catalog number: CL0310-2), 50 μL of the supernatant was transferred to the CLIA assay plate and 50 μL of enzyme conjugate reagent was added into each well. The plates were sealed and gently agitated for 1 hour at room temperature. The supernatant-enzyme-mixture was discarded and wells were washed 6 times with 300 μL of PBS. The residual liquid was removed by plating the CLIA plate right side down on absorbent tissue paper. 25 μL of substrates A and B were added to each well. Luminance was measured using a luminometer (Mithras LB 940 Multimode Microplate Reader) after 10 minutes incubation. Dose-response curves were generated and the IC$_{50}$ value was extrapolated by using the E-WorkBook Suite (ID Business Solutions Ltd., Guildford, UK). The IC$_{50}$ was defined as the compound concentration (or conditioned media log dilution) at which HBsAg secretion was reduced by 50% compared to the no drug control.

The compounds according to formula I were tested for their capacity to inhibit HBsAg as described herein. The Examples were tested in the above assay and found to have IC$_{50}$ below 50 μM. Particular compounds of formula I were found to have IC$_{50}$ below 1.0 μM. Results of HBsAg assay are given in Table 1.

TABLE 1

| List of Activity data | |
| --- | --- |
| Example No. | IC$_{50}$ (μM) |
| 1 | 18.707 |
| 2 | 2.534 |
| 3 | 0.74 |
| 4 | 26.068 |
| 5 | 0.248 |
| 6 | 0.053 |
| 7 | 0.172 |
| 8 | 0.044 |
| 9 | 0.624 |
| 10 | 0.225 |
| 11 | 0.039 |
| 12 | 9.428 |
| 13 | 0.11 |
| 14 | 0.047 |
| 15 | 0.5 |

We claim:
1. A compound of formula I,

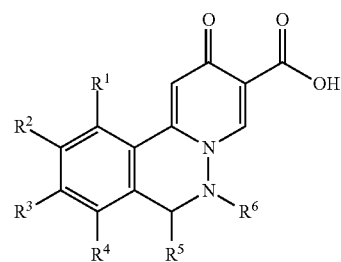

wherein
R$^1$, R$^2$, R$^3$ and R$^4$ are independently selected from C$_{1-6}$alkyl, haloC$_{1-6}$alkyl, hydrogen, halogen, amino, cyano, pyrrolidinyl, hydroxy, C$_{1-6}$alkoxy, haloC$_{1-6}$alkoxy, C$_{3-7}$cycloalkylC$_{1-6}$alkyloxy, phenylC$_{1-6}$alkyloxy, hydroxyC$_{1-6}$alkyloxy, C$_{1-6}$alkoxyC$_{1-6}$alkyloxy, C$_{1-6}$alkylsulfanylC$_{1-6}$alkyloxy, C$_{1-6}$alkylsulfonylC$_{1-6}$alkyloxy, cyanoC$_{1-6}$alkyloxy, aminoC$_{1-6}$alkyloxy, C$_{1-6}$alkylaminoC$_{1-6}$alkyloxy, diC$_{1-6}$alkylaminoC$_{1-6}$alkyloxy, C$_{1-6}$alkylcarbonylaminoC$_{1-6}$alkyloxy, C$_{1-6}$alkylsulfonylaminoC$_{1-6}$alkyloxy, C$_{1-6}$alkoxycarbonylaminoC$_{1-6}$alkyloxy, pyrazolylC$_{1-6}$alkyloxy, triazolylC$_{1-6}$alkyloxy and monocyclic heterocycloalkylC$_{1-6}$alkyloxy, wherein monocyclic heterocycloalkyl is N-containing monocyclic heterocycloalkyl;
R$^5$ and R$^6$ are independently selected from hydrogen, C$_{1-6}$alkyl, haloC$_{1-6}$alkyl or C$_{2-6}$alkenyl;
or a pharmaceutically acceptable salt, or an enantiomer, or a diastereomer thereof.
2. The compound of formula I according to claim 1, wherein
R$^1$ is hydrogen;
R$^2$ is C$_{1-6}$alkoxy;
R$^3$ is C$_{1-6}$alkoxy, haloC$_{1-6}$alkoxy, hydroxyC$_{1-6}$alkoxy, C$_{1-6}$alkoxyC$_{1-6}$alkyloxy, C$_{1-6}$alkylsulfonylC$_{1-6}$alkoxy, cyanoC$_{1-6}$alkoxy, carboxyC$_{1-6}$alkoxy, aminoC$_{1-6}$alkoxy, C$_{1-6}$alkoxycarbonylaminoC$_{1-6}$alkoxy, morpholinylC$_{1-6}$alkoxy or tetrahydropyranylC$_{1-6}$alkoxy;
R$^4$ is hydrogen;
R$^5$ is hydrogen;
R$^6$ is hydrogen, C$_{1-6}$alkyl or C$_{2-6}$alkenyl;

or a pharmaceutically acceptable salt, or an enantiomer, or diastereomer thereof.

3. A compound of formula I according to claim 2, wherein $R^2$ is methoxy;
$R^3$ methoxy, trifluoroethoxy, hydroxydimethylpropoxy, methoxypropoxy, methylsulfonylpropoxy, cyanopropoxy, carboxybutoxy, aminopentoxy, tert-butoxycarbonylaminopentoxy, morpholinylethoxy or tetrahydropyranylmethoxy;
$R^6$ is hydrogen, methyl, isopropyl, isobutyl or prop-2-enyl;
or a pharmaceutically acceptable salt, or an enantiomer, or a diastereomer thereof.

4. The compound of formula I according to claim 1, or a pharmaceutically acceptable salt, or an enantiomer, or a diastereomer thereof, wherein $R^2$ is methoxy.

5. The compound of formula I according to claim 1, or a pharmaceutically acceptable salt, or an enantiomer, or a diastereomer thereof, wherein $R^3$ is halo$C_{1-6}$alkoxy, hydroxy$C_{1-6}$alkoxy, $C_{1-6}$alkoxy$C_{1-6}$alkyloxy, cyano$C_{1-6}$alkoxy, $C_{1-6}$alkoxycarbonylamino$C_{1-6}$alkoxy or tetrahydropyranyl$C_{1-6}$alkoxy.

6. The compound of formula I according to claim 5, or a pharmaceutically acceptable salt, or an enantiomers, or a diastereomer thereof, wherein $R^3$ is trifluoroethoxy, hydroxydimethylpropoxy, methoxypropoxy, cyanopropoxy, tert-butoxycarbonylaminopentoxy, or tetrahydropyranylmethoxy.

7. The compound of formula I according to claim 1, or pharmaceutically acceptable salts, or enantiomers, or diastereomer thereof, wherein $R^6$ is $C_{1-6}$alkyl.

8. The compound of formula I according to claim 7, or a pharmaceutically acceptable salt, or an enantiomers, or a diastereomer thereof, wherein $R^6$ is isobutyl.

9. The compound according to claim 1, which compound is selected from the group consisting of:
9,10-Dimethoxy-2-oxo-6,7-dihydropyrido[2,1-a]phthalazine-3-carboxylic acid;
9,10-Dimethoxy-6-methyl-2-oxo-7H-pyrido[2,1-a] phthalazine-3-carboxylic acid;
6-Allyl-9,10-dimethoxy-2-oxo-7H-pyrido[2,1-a]phthalazine-3-carboxylic acid;
6-Isopropyl-9,10-dimethoxy-2-oxo-7H-pyrido[2,1-a] phthalazine-3-carboxylic acid;
6-Isobutyl-9,10-dimethoxy-2-oxo-7H-pyrido[2,1-a] phthalazine-3-carboxylic acid;
6-Isobutyl-10-methoxy-9-(3-methoxypropoxy)-2-oxo-7H-pyrido[2,1-a]phthalazine-3-carboxylic acid;
6-Isobutyl-10-methoxy-2-oxo-9-(2,2,2-trifluoroethoxy)-7H-pyrido[2,1-a]phthalazine-3-carboxylic acid;
6-Isobutyl-10-methoxy-2-oxo-9-(tetrahydropyran-4-ylmethoxy)-7H-pyrido[2,1-a]phthalazine-3-carboxylic acid;
6-Isobutyl-10-methoxy-9-(3-methylsulfonylpropoxy)-2-oxo-7H-pyrido[2,1-a]phthalazine-3-carboxylic acid;
6-Isobutyl-10-methoxy-9-(2-morpholinoethoxy)-2-oxo-7H-pyrido[2,1-a]phthalazine-3-carboxylic acid;
9-(3-Hydroxy-2,2-dimethyl-propoxy)-6-isobutyl-10-methoxy-2-oxo-7H-pyrido[2,1-a]phthalazine-3-carboxylic acid;
9-(4-Carboxybutoxy)-6-isobutyl-10-methoxy-2-oxo-7H-pyrido[2,1-a]phthalazine-3-carboxylic acid;
9-(3-Cyanopropoxy)-6-isobutyl-10-methoxy-2-oxo-7H-pyrido[2,1-a]phthalazine-3-carboxylic acid;
9-[5-(Tert-butoxycarbonylamino)pentoxy]-6-isobutyl-10-methoxy-2-oxo-7H-pyrido[2,1-a]phthalazine-3-carboxylic acid; and,
9-(5-Aminopentoxy)-6-isobutyl-10-methoxy-2-oxo-7H-pyrido[2,1-a]phthalazine-3-carboxylic acid hydrochloride; or,
a pharmaceutically acceptable salt, or an enantiomers, or a diastereomer thereof.

10. The compound according to claim 9, which compound is selected from the group consisting of:
6-Isobutyl-10-methoxy-9-(3-methoxypropoxy)-2-oxo-7H-pyrido[2,1-a]phthalazine-3-carboxylic acid;
6-Isobutyl-10-methoxy-2-oxo-9-(tetrahydropyran-4-ylmethoxy)-7H-pyrido[2,1-a]phthalazine-3-carboxylic acid;
9-(3-Hydroxy-2,2-dimethyl-propoxy)-6-isobutyl-10-methoxy-2-oxo-7H-pyrido[2,1-a]phthalazine-3-carboxylic acid; and,
9-[5-(Tert-butoxycarbonylamino)pentoxy]-6-isobutyl-10-methoxy-2-oxo-7H-pyrido[2,1-a]phthalazine-3-carboxylic acid; or,
a pharmaceutically acceptable salt, or an enantiomer, or a diastereomer thereof.

11. A process for the preparation of a compound according to claim 1 comprising hydrolysis of a compound of formula (A) to afford a compound of formula (I)

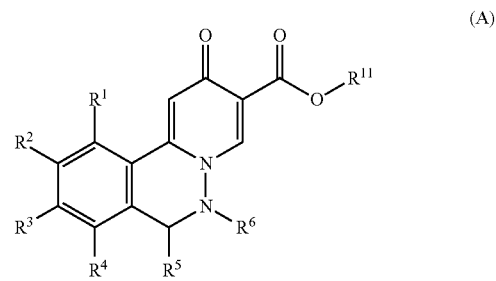

(A)

wherein $R^{11}$ is $C_{1-6}$ alkyl.

12. The process of according to claim 11 wherein $R^3$ is —$C_{1-6}$alkoxy, halo$C_{1-6}$alkoxy, $C_{3-7}$cycloalkyl$C_{1-6}$alkyloxy, phenyl$C_{1-6}$alkyloxy, hydroxy$C_{1-6}$alkyloxy, $C_{1-6}$alkoxy$C_{1-6}$alkyloxy, $C_{1-6}$alkylsulfanyl$C_{1-6}$alkyloxy, $C_{1-6}$alkylsulfonyl$C_{1-6}$alkyloxy, cyano$C_{1-6}$alkyloxy, amino$C_{1-6}$alkyloxy, $C_{1-6}$alkylamino$C_{1-6}$alkyloxy, di$C_{1-6}$alkylamino$C_{1-6}$alkyloxy, $C_{1-6}$alkylcarbonylamino$C_{1-6}$alkyloxy, $C_{1-6}$alkylsulfonylamino$C_{1-6}$alkyloxy, $C_{1-6}$alkoxycarbonylamino$C_{1-6}$alkyloxy, pyrazolyl$C_{1-6}$alkyloxy, triazolyl$C_{1-6}$alkyloxy and monocyclic heterocycloalkyl$C_{1-6}$alkyloxy, wherein monocyclic heterocycloalkyl is N-containing monocyclic heterocycloalkyl.

13. A pharmaceutical composition comprising a compound in accord with claim 1 and at least one pharmaceutically acceptable carrier, diluent or excipient.

14. The method of inhibiting HBsAg production or secretionin a cell comprising treating the cell with a therapeutically effective amount of a compound according to claim 1.

15. A method for the treatment or prophylaxis of HBV infection, which method comprises administering to a patient in need thereof a therapeutically effective amount of a compound according to claim 1.

* * * * *